US005663320A

United States Patent [19]
Mansour et al.

[11] Patent Number: 5,663,320
[45] Date of Patent: Sep. 2, 1997

[54] PROCESSES FOR THE DIASTEREOSELECTIVE SEPARATION OF NUCLEOSIDE ANALOGUE SYNTHETIC INTERMEDIATES

[75] Inventors: Tarek Mansour, Montreal; Haolun Jin, Pierrefonds; Allan H.L. Tsé, St-Laurent; M. Arshad Siddiqui, St-Laurent, all of Canada

[73] Assignee: BioChem Pharma, Inc., Laval, Canada

[21] Appl. No.: 460,856

[22] Filed: Jun. 5, 1995

Related U.S. Application Data

[60] Division of Ser. No. 142,387, Jun. 13, 1994, which is a continuation-in-part of Ser. No. 703,379, May 21, 1991, abandoned.

[51] Int. Cl.$^6$ .......................... C07H 19/00; C07D 333/32; C07D 333/34
[52] U.S. Cl. .................... 536/27.11; 549/63; 549/62; 549/430; 536/4.1
[58] Field of Search ...................... 536/27.11, 4.1; 549/63, 430

[56] References Cited

U.S. PATENT DOCUMENTS

| | | | |
|---|---|---|---|
| 4,231,945 | 11/1980 | McCombie | 549/475 |
| 4,383,114 | 5/1983 | Vince | 544/277 |
| 5,204,466 | 4/1993 | Liotta et al. | 544/317 |
| 5,210,085 | 5/1993 | Liotta et al. | 514/274 |

FOREIGN PATENT DOCUMENTS

| | | |
|---|---|---|
| 0 071 926 | 2/1983 | European Pat. Off. |
| 0 266 042 A | 4/1988 | European Pat. Off. |
| 0349242 | 1/1990 | European Pat. Off. |
| 0 382 526 A | 2/1990 | European Pat. Off. |
| 0 337 713 A | 8/1990 | European Pat. Off. |
| 0 515 156 A1 | 5/1992 | European Pat. Off. |
| 0 515 157 A1 | 5/1992 | European Pat. Off. |
| 1445013 | 5/1966 | France . |
| 9111186 | 8/1991 | WIPO . |
| WO 91/17159 | 11/1991 | WIPO . |
| WO 92/10496 | 6/1992 | WIPO . |
| WO 92/14743 | 9/1992 | WIPO . |
| WO 92/18517 | 10/1992 | WIPO . |
| WO 92/19246 | 11/1992 | WIPO . |
| WO 92/20696 | 11/1992 | WIPO . |

OTHER PUBLICATIONS

Goodman, "Chemical Syntheses and Transformations of Nucleosides," in *Basic Principles in Nucleic Ac id Chemistry*, vol. 1, Academic Press, New York, 1974, pp. 106–110.

March, *Advanced Organic Chemistry*, McGraw-Hill Book Co., New York, 1968, pp. 896–897.

M. Fieser, *Reagents for Organic Synthesis*, vol. 8, Wiley-Interscience, New York, 1980, pp. 261–263.

M. Fieser, *Reagents for Organic Synthesis*, vol. 12, Wiley-Interscience, New York, 1986, pp. 543–547.

Chu et al., "Synthesis and Structure–Activity Relationships of 6–Substituted 2',3'-Dideoxypurine Nucleosides as Potential Anti–Human Immunodeficiency Virus Agents," *J. Med. Chem.*, 33(6), 1553–1561 (1990).

Farina et al., "a New Synthesis of 2',3'-Dideoxynucleosides for AIDS Chemotherapy," *Tett. Letters*, 29(11), 1239–1242 (1988).

Mansuri et al., "Preparation of the Geometric Isomers of DDC, DDA, D4C and D4T as Potential Anti–HIV Agents," *Bioorganic & Medicinal Chem. Letters*, 1(1), 65–68 (1991).

Vince et al., "Synthesis of Anti–HIV Activity of Carbocyclic 2',3'-Didehydro-2',3'-dideoxy-2,6-Disubstituted Purine Nucleosides," *J. Medicinal Chem.*, 33(1), 17–21 (1990).

Wilson et al., "The Synthesis and Anti–HIV Activity of Pyrimidinyl Dioxolanyl Nucleosides", *Bioorganic & Medicinal Chem. Letters*, 3(2), 169–174 (1993).

J.W. Beach et al., "Synthesis of Enantiomerically Pure (2',R,5+s)–(–)–1–[2–(hydroxymethyl)oxathiolan–5–yl]cytosine as a Potent Antiviral Agent Against Hepatitis B Virus (HBV) and Human Immunodeficiency Virus (HIV)", *J. Org. Chem.*, vol. 57, pp. 2217–2219 (1992).

B.R. Belleau, et al., "Oxidative Degradation of L–Ascorbic Acid Acetals to 2',3'-Dideoxy-3'-Oxaribofuranosides. Synthesis of Enantiomerically Pure 2',3'-Dideoxy-3'-Oxacytidine Stereoisomers as Potential Antiviral Agents", *Tetrahedron Lett.*, vol. 33, pp. 6949–6952 (1992).

W–B. Choi, et al., "In Situ Complexation Directs the Stereochemistry of N–Glycoslylation in the Synthesis of Oxathiolanyl and Dioxolanyl Nucleoside Analogues", *J. Am. Chem. Soc.*, vol. 113, pp. 9377–9379 (1991).

W–B. Choi, et al., "Synthesis, Anti–Human Immunodeficiency Virus, and Anti–Hepatitis B Virus Activity of Pyrimidine Oxathiolane Nucleosides", *Bioorg. & Med. Chem. Lett.*, vol. 3(4), pp. 693–696 (1993).

C.K. Chu et al., "Enantiomeric Synthesis of (+)–BCH–189 [(+)–(2S,5R)–1–[2–(Hydroxymethyl)–1",3–oxathiolan–5–yl]cytosine] from D–Mannose and Its Anti–HIV Activity", *J. Org. Chem.*, vol. 56, pp. 6503–6505 (1991).

P. Faury, et al., "Synthesis of Tetrazole Oxathiolane Nucleoside Analogues and Their Evaluation of HIV–1 Antiviral Agents", *Nucleosides & Nucleotides*, vol. 11(8), pp. 1481–1488 (1992).

G. Hesse et al., "Mercapto–acetaldehyd und Dioxy–1, 4–dithian", *Chem. Ber.*, vol. 85, pp. 924–932 (1952).

D.C. Humber et al., "Expeditious Preparation of (–)–2'–Deoxy–3'–Thiacytidine (3TC)", *Tetrahedron Lett.*, vol. 33, pp. 4625–4628 (1992).

(List continued on next page.)

*Primary Examiner*—John Kight
*Assistant Examiner*—L. Eric Crane
*Attorney, Agent, or Firm*—Fish & Neave; James F. Haley, Jr.; Leslie A. McDonell

[57] ABSTRACT

The present invention relates to highly diastereoselective processes for production of cis-nucleosides and nucleoside analogues and derivatives in high optical purity and intermediates useful in those processes.

3 Claims, No Drawings

OTHER PUBLICATIONS

L.S. Jeong, et al., "An Efficient Synthesis of Enantiomerically Pure (+)-(2S,5R)-1-[2-(Hydroxymethyl)-1,3-Oxathiolan-5-yl)cytosine (+)-BCH-189] from D-Galactose", *Tetrahedron Lett.*, vol. 33, pp. 595-598 (1992).

L.S. Jeong, et al., "Asymmetric Synthesis and Biological Evaluation of β-L-(2R,5S)-and α-L-(2R,5R)-1,3-Oxathiolane-Pyrimidine and -Purine Nucleosides as Potential Anti-HIV Agents", *J. Med. Chem.*, vol. 36, pp. 181-195 (1993).

L.S. Jeong, et al., "Structure-Activity Relationships of β-D-(2S,5R)-and α-D-(2S,5S)-1,3-Oxoathiolanyl Nucleosides as Potential Anti-HIV Agents", *J. Med. Chem.*, vol. 36, pp. 2627-2638 (1993).

H. Jin, et al., "Unexpected Effects of Lewis Acids in the Synthesis of Optically Pure 2'-Deoxy-3'-Oxayctidine Nucleoside Analogues", *Tetrahedron: Asymmetry*, vol. 4(2), pp. 211-214 (1993).

J.L. Kraus, et al., "Synthesis of New 2,5-Disubstituted 1,3-Oxathiolanes. Intermediates in Nucleoside Chemistry", *Synthesis*, pp. 1046-1048 (1991).

J.M. McIntosh et al., "2-Mercaptoaldehyde Dimers and 2,5-Dihydrothiophenes From 1,3-Oxathiolan-5-ones", *Can J. Chem.*, vol. 61, pp. 1872-1875 (1983).

R. Storer et al., "The Resolution and Absolute Stereochemistry of the Enantiomers of cis-1-[2-(Hydroxymethyl)-1,3-Oxathiolan-5-yl]Cytosine (BCH-189): Equipotent Anti-HIV Agents", *Nucleosides & Nucleotides*, vol. 12, pp. 225-236 (1993).

E. Vedejs, et al., "Method for Sulfide S-Benzylation or S-Allylation Using Trimethylsilyl Triflate Activated Benzyl or Allyl Ethers", *J. Org. Chem.*, vol. 46, pp. 3353-3354 (1981).

PROCESSES FOR THE DIASTEREOSELECTIVE SEPARATION OF NUCLEOSIDE ANALOGUE SYNTHETIC INTERMEDIATES

CROSS REFERENCE TO RELATED APPLICATIONS

This application is a division of application Ser. No. 08/142,387, filed Jun. 13, 1994, which is a continuation-in-part of application Ser. No. 07/703,379, filed May 21, 1991, now abandoned.

FIELD OF THE INVENTION

The present invention relates to diastereoselective processes for preparing optically active cis-nucleosides and nucleoside analogues and derivatives. The novel processes of this invention allow the stereo-controlled synthesis of a given enantiomer of a desired cis-nucleoside or nucleoside analogue or derivative in high optical purity. This invention also relates to novel intermediates useful in the processes of this invention.

BACKGROUND OF THE INVENTION

Nucleosides and their analogues and derivatives are an important class of therapeutic agents. For example, a number of nucleosides have shown antiviral activity against retroviruses such as human immunodeficiency virus (HIV), hepatitis B virus (HBV) and human T-lymphotropic virus (HTLV) (PCT publication WO 89/04662 and European Patent publication 0349242 A2). Among the nucleosides shown to have antiviral activity are 3'-azido-3'-deoxythymidine (AZT), 2'3'-dideoxy-cytidine (DDC), 2-hydroxymethyl-5-(cytosin-1'-yl)-1,3-oxathiolane and 2-hydroxymethyl-4-(guanin-9'-yl)-1,3-dioxolane (European Patent publication 0382526 A2 and European Patent publication 0377713 A2).

Most nucleosides and nucleoside analogues and derivatives contain at least two chiral centers (shown as * in formula (A)), and exist in the form of two pairs of optical isomers (i.e., two in the cis-configuration and two in the trans-configuration). However, generally only the cis-isomers exhibit useful biological activity.

Different enantiomeric forms of the same cis-nucleoside may, however, have very different antiviral activities. M. M. Mansuri et al., "Preparation Of The Geometric Isomers Of DDC, DDA, D4C and D4T As Potential Anti-HIV Agents", *Bioorg.Med.Chem.Lett.*, 1 (1), pp. 65–68 (1991). Therefore, a general and economically attractive stereoselective synthesis of the enantiomers of the biologically active cis-nucleosides is an important goal.

Many of the known processes for producing optically active nucleosides and their analogues and derivatives modify naturally occurring (i.e., optically active) nucleosides by altering the base or by altering the sugar via reductive procedures such as deoxygenation or radical initiated reductions. C. K. Chu et al., "General Synthesis Of 2',3'-Dideoxynucleosides And 2',3'-Didehydro-2',3'-Dideoxynucleosides," *J.Org.Chem.*, 54, pp. 2217–2225 (1989). These transformations involve multiple steps, including protection and deprotection and usually result in low yields. Moreover, they begin with and maintain the optical activity of the starting nucleoside. Thus, the nucleosides produced by these processes are limited to specific analogues of the enantiomeric form of the naturally occurring nucleoside. In addition, these procedures require the availability of the naturally occurring nucleoside, often an expensive starting material.

Other known processes for producing optically active nucleosides rely on conventional glycosylation procedures to add the sugar to the base. These procedures invariably give anomeric mixtures of cis- and trans-isomers which require tedious separation and result in lower yields of the desired biologically active cis-nucleoside. Improved glycosylation methods designed to yield only the cis-nucleoside require addition of a 2'- or 3'-substituent to the sugar. Because the 2'- or 3'-substituent is only useful in controlling cis-nucleoside synthesis in one configuration (when the 2' or 3' substituent is trans- to the 4' substituent), multiple steps are required to introduce this substituent in the proper configuration. The 2'- or 3'-substituent must then be removed after glycosylation, requiring additional steps. L. Wilson and D. Liotta, "A General Method For Controlling Stereochemistry In The Synthesis Of 2'-Deoxyribose Nucleosides", *Tetrahedron Lett.*, 31, pp. 1815–1818 (1990). Furthermore, to obtain an optically pure nucleoside product, the starting sugar must be optically pure. This also requires a series of time-consuming syntheses and purification steps.

SUMMARY OF THE INVENTION

The present invention overcomes the difficulties and shortcomings of the prior art and provides processes for producing optically active cis-nucleosides (1,3-oxathiolanes, 2,4-dioxolanes, and 1,3-dithiolanes) or nucleoside analogues and derivatives of formula (I)

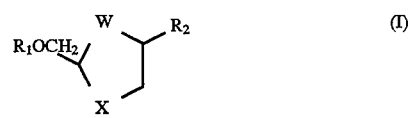

wherein W is S, S=O, $SO_2$, or O;

X is S, S=O, $SO_2$, or O;

$R_1$ is hydrogen or acyl; and $R_2$ is a purine or pyrimidine base or an analogue or derivative thereof.

The processes of this invention comprise the step of glycosylating a desired purine or pyrimidine base or analogue or derivative thereof with an intermediate of formula (IIa) or (IIb)

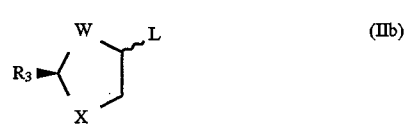

wherein $R_3$ is a substituted carbonyl or carbonyl derivative and L is a leaving group. Glycosylation is accomplished using a Lewis acid of the formula (III)

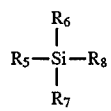

wherein $R_5$, $R_6$, $R_7$, and $R_8$ are defined below and the resulting intermediate is reduced to give a nucleoside or nucleoside analogue or derivative of formula (I).

The processes of this invention have the advantages of allowing preparation of a nucleoside of formula (I) (or analogues or derivatives thereof) without using expensive starting materials, cumbersome protection and deprotection steps or addition and removal of 2'- or 3'-substituents. The processes of this invention produce nucleosides in high yields, with high purity and high optical specificity. The processes of this invention have the further advantage of generating nucleosides whose stereoisomeric configuration can be easily controlled simply by the selection of the appropriate starting materials.

DETAILED DESCRIPTION OF THE INVENTION

In the processes for preparing optically active compounds of this invention in a configurational- and diastereo-selective manner, the following definitions are used:

$R_2$ is a purine or pyrimidine base or an analogue or derivative thereof.

A purine or pyrimidine base is a purine or pyrimidine base found in naturally occurring nucleosides. An analogue thereof is a base which mimics such naturally occurring bases in that their structures (the kinds of atoms and their arrangement) are similar to the naturally occurring bases but may either possess additional or lack certain of the functional properties of the naturally occurring bases. Such analogues include those derived by replacement of a CH moiety by a nitrogen atom, e.g., 5-azapyrimidines such as 5-azacytosine) or vice versa (e.g., 7-deazapurines, such as 7-deazaadenine or 7-deazaguanine) or both (e.g., 7-deaza, 8-azapurines). By derivatives of such bases or analogues are meant those bases wherein ring substituents are either incorporated, removed, or modified by conventional substituents known in the art, e.g., halogen, hydroxyl, amino, $C_{1-6}$ alkyl. Such purine or pyrimidine bases, analogues and derivatives are well known to those skilled in the art.

A "nucleoside analogue or derivative" is a 1,3-oxathiolane, 2,4-dioxolane or 1,3-dithiolane which has been modified in any of the following or combinations of the following ways: base modifications, such as addition of a substituent (e.g., 5-fluorocytosine) or replacement of one group by an isosteric group (e.g., 7-deazaadenine); sugar modifications, such as substitution of the C-2 and C-3 hydroxyl groups by any substituent, including hydrogen (e.g., 2',3'-dideoxynucleosides); alteration of the site of attachment of the sugar to the base (e.g., pyrimidine bases usually attached to the sugar at the N-1 site may be, for example, attached at the N-3 or C-6 site and purines usually attached at the N-9 site may be, for example, attached at N-7); alteration of the site of attachment of the base to the sugar (e.g., the base may be attached to the sugar at C-2, such as iso-DDA); or alteration of configuration of the sugar-base linkage (e.g., cis or trans configurations).

$R_3$ is a carbonyl substituted with hydrogen, hydroxyl, trialkylsilyl, trialkylsiloxy, $C_{1-30}$ alkyl, $C_{7-30}$ aralkyl, $C_{1-30}$ alkoxy, $C_{1-30}$ amine (primary, secondary or tertiary), $C_{1-30}$ thiol; $C_{6-20}$ aryl; $C_{1-20}$ alkenyl; $C_{1-20}$ alkynyl; 1,2-dicarbonyl, such as

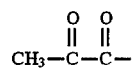

substituted with $C_{1-6}$ alkyl or $C_{6-20}$ aryl; anhydrides such as

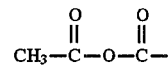

substituted with $C_{1-6}$ alkyl or $C_{6-20}$ aryl; azomethine substituted at nitrogen with hydrogen, $C_{1-20}$ alkyl or $C_{1-10}$ alkoxy or $C_{1-10}$ dialkylamino or at carbon with hydrogen, $C_{1-20}$ alkyl, or $C_{1-20}$ alkoxy; thiocarbonyl (C=S) substituted with hydroxyl, $C_{1-20}$ alkoxy, or $C_{1-20}$ thiol; a homologue of carbonyl, e.g.,

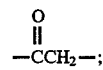

a homologue of thiocarbonyl, e.g.,

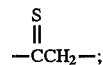

or a homologue of azomethine, such as

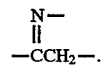

The preferred substituted carbonyl/carbonyl derivatives are alkoxycarbonyls, such as methyl, ethyl, isopropyl, t-butyl and menthyl; carboxyls, diethylcarboxamide; pyrrolidine amide; methyl ketone and phenyl ketone. The more preferred substituted carbonyl/carbonyl derivatives are esters and carboxyls and the most preferred are esters.

$R_4$ is a chiral auxiliary. The term "chiral auxiliary" describes asymmetric molecules that are used to effect the chemical resolution of a racemic mixture. Such chiral auxiliaries may possess one chiral center such as methylbenzylamine or several chiral centers such as menthol. The purpose of the chiral auxiliary, once built into the starting material, is to allow simple separation of the resulting diastereomeric mixture. See, for example, J. Jacques et al., *Enantiomers, Racemates And Resolutions*, pp. 251–369, John Wiley & Sons, New York (1981).

$R_5$, $R_6$ and $R_7$ are independently selected from the group consisting of hydrogen, $C_{1-20}$ alkyl (e.g., methyl, ethyl, t-butyl), optionally substituted by halogens (F, Cl, Br, I), $C_{6-20}$ alkoxy (e.g., methoxy) or $C_{6-20}$ aryloxy (e.g., phenoxy); $C_{7-20}$ aralkyl (e.g., benzyl), optionally substituted by halogen, $C_{1-20}$ alkyl or $C_{1-20}$ alkoxy (e.g., p-methoxybenzyl); $C_{6-20}$ aryl (e.g., phenyl), optionally substituted by halogens, $C_{1-20}$ alkyl or $C_{1-20}$ alkoxy; trialkylsilyl; halogens (F, Cl, Br, I).

$R_8$ is selected from the group consisting of halogen (F, Cl, Br, I); $C_{1-20}$ sulphonate esters, optionally substituted by halogens (e.g., trifluoromethane sulphonate); $C_{1-20}$ alkyl esters, optionally substituted by halogen (e.g., trifluoroacetate); polyvalent halides (e.g., triiodide); trisubstituted silyl groups of the general formula $(R_5)(R_6)(R_7)Si$ (wherein $R_5$, $R_6$, and $R_7$ are as defined above); saturated or unsaturated selenenyl $C_{6-20}$ aryl; substituted or unsubstituted $C_{6-20}$ arylsulfenyl; substituted or unsubstituted $C_{1-20}$ alkoxyalkyl; and trialkylsiloxy.

L is a "leaving group", i.e., an atom or a group which is displaceable upon reaction with an appropriate purine or pyrimidine base, with or without the presence of a Lewis acid. Suitable leaving groups include acyloxy groups, alkoxy groups, e.g., alkoxy carbonyl groups such as ethoxy carbonyl; halogens such as iodine, bromine, chlorine, or fluorine; amido; azido; isocyanato; substituted or unsubstituted, saturated or unsaturated thiolates, such as thiomethyl or thiophenyl; substituted or unsubstituted, saturated or unsaturated seleno, seleninyl, or selenonyl compounds, such as phenyl selenide or alkyl selenide.

A suitable leaving group may also be —OR, where R is a substituted or unsubstituted, saturated or unsaturated alkyl group, e.g., $C_{1-6}$ alkyl or alkenyl group; a substituted or unsubstituted aliphatic or aromatic acyl group, e.g., a $C_{1-6}$ aliphatic acyl group such as acetyl and a substituted or unsubstituted aromatic acyl group such as benzoyl; a substituted or unsubstituted, saturated or unsaturated alkoxy or aryloxy carbonyl group, such as methyl carbonate and phenyl carbonate; substituted or unsubstituted sulphonyl imidazolide; substituted or unsubstituted aliphatic or aromatic amino carbonyl group, such as phenyl carbamate; substituted or unsubstituted alkyl imidiate group such as trichloroacetamidate; substituted or unsubstituted, saturated or unsaturated phosphonate, such as diethylphosphonate; substituted or unsubstituted aliphatic or aromatic sulphinyl or sulphonyl group, such as tosylate; or hydrogen.

As used in this application, the term "alkyl" represents a substituted (by a halogen, hydroxyl or $C_{6-20}$ aryl) or unsubstituted straight chain, branched chain, or cyclic hydrocarbon moiety having 1 to 30 carbon atoms and preferably, from 1 to 6 carbon atoms.

The terms "alkenyl" and "alkynyl" represent substituted (by a halogen, hydroxyl or $C_{6-20}$ aryl) or unsubstituted straight, branched or cyclic hydrocarbon chains having 1 to 20 carbon atoms and preferably from 1 to 5 carbon atoms and containing at least one unsaturated group (e.g., allyl).

The term "alkoxy" represents a substituted or unsubstituted alkyl group containing from 1 to 30 carbon atoms and preferably from 1 to 6 carbon atoms, wherein the alkyl group is covalently bonded to an adjacent element through an oxygen atom (e.g., methoxy and ethoxy).

The term "amine" represents alkyl, aryl, alkenyl, alkynyl, or aralkyl groups containing from 1 to 30 carbon atoms and preferably 1 to 12 carbon atoms, covalently bonded to an adjacent element through a nitrogen atom (e.g., pyrrolidine). They include primary, secondary and tertiary amines and quaternary ammonium salts.

The term "thiol" represents alkyl, aryl, aralkyl, alkenyl or alkynyl groups containing from 1 to 30 carbon atoms and preferably from 1 to 6 carbon atoms, covalently bonded to an adjacent element through a sulfur atom (e.g., thiomethyl).

The term "aryl" represents a carbocyclic moiety which may be substituted by at least one heteroatom (e.g., N, O, or S) and containing at least one benzenoid-type ring and preferably containing from 6 to 15 carbon atoms (e.g., phenyl and naphthyl).

The term "aralkyl" represents an aryl group attached to the adjacent atom by an alkyl (e.g., benzyl).

The term "alkoxyalkyl" represents an alkoxy group attached to the adjacent group by an alkyl group (e.g., methoxymethyl).

The term "aryloxy" represents a substituted (by a halogen, trifluoromethyl or $C_{1-5}$ alkoxy) or unsubstituted aryl moiety covalently bonded through an oxygen atom (e.g., phenoxy).

The term "acyl" refers to a radical derived from a carboxylic acid, substituted (by a halogen (F, Cl, Br, I), $C_{6-20}$ aryl or $C_{1-6}$ alkyl) or unsubstituted, by replacement of the —OH group. Like the acid to which it is related, an acyl radical may be aliphatic or aromatic, substituted (by a halogen, $C_{1-5}$ alkoxyalkyl, nitro or $O_2$) or unsubstituted, and whatever the structure of the rest of the molecule may be, the properties of the functional group remain essentially the same (e.g., acetyl, propionyl, isobutanoyl, pivaloyl, hexanoyl, trifluoroacetyl, chloroacetyl, and cyclohexanoyl).

A key feature of the processes of this invention is the use of a substituted carbonyl or carbonyl derivative as $R_3$ instead of a protected hydroxymethyl group as previously described in the art. Surprisingly, the substituted carbonyl or carbonyl derivative is not cleaved by exposure to a Lewis acid, as would have been expected by one of skill in the art when a Lewis acid of formula (III) is added to a mixture of silylated purine or pyrimidine base and the chiral auxiliary-sugar compound obtained in Step 3. Instead, the substituted carbonyl/carbonyl derivative in the intermediate of formula (VI) forces the purine or pyrimidine base ($R_2$) to add in the cis-configuration relative to the substituted carbonyl/carbonyl derivative group. Without a substituted carbonyl or carbonyl derivative attached to C4' (for example, when a hydroxymethyl group is instead used), the coupling procedures described in Step 4 will result in a mixture of cis- and trans-isomers.

Another key feature of the processes of this invention is the choice of Lewis acid. The Lewis acids used in the preparation of compounds of formula (I) have the general formula (III)

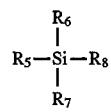

wherein $R_5$, $R_6$, $R_7$ and $R_8$ are as defined previously. These Lewis acids may be generated in situ or prepared using any method known in the art (e.g., A. H. Schmidt, "Bromotrimethylsilane and Iodotrimethylsilane-Versatile Reagents for Organic Synthesis", *Aldrichimica Acta*, 14, pp. 31–38 (1981). The preferred Lewis acids of this invention are iodotrimethylsilane and trimethylsilyl triflate. The preferred $R_5$, $R_6$ and $R_7$ groups are methyl or iodine. The most preferred $R_5$, $R_6$ and $R_7$ group is methyl. The preferred $R_8$ groups are iodine, chlorine, bromine or sulphonate esters. The most preferred $R_8$ groups are iodine and trifluoromethane sulphonate.

In the preferred process of this invention, illustrated in Schemes 1 and 2, cis- and trans-isomers of a sugar of formula (II)

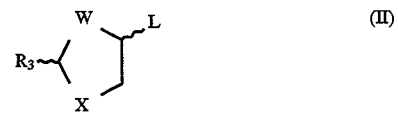

are separated by fractional crystallization and the desired configurational isomer selected. The selected cis- or the trans-isomer may then be resolved chemically, e.g., using a chiral auxiliary, enzymatically, or by other methods known in the art. The pure diastereomer is then coupled to a silylated purine or pyrimidine base in the presence of a Lewis acid to afford an optically active nucleoside of cis-configuration which is subsequently reduced to give a nucleoside of formula (I).

Schemes 1A and 1B depict this preferred process as applied to any 1,3-oxathiolane, 2,4-dioxolane or 1,3-dithiolane.

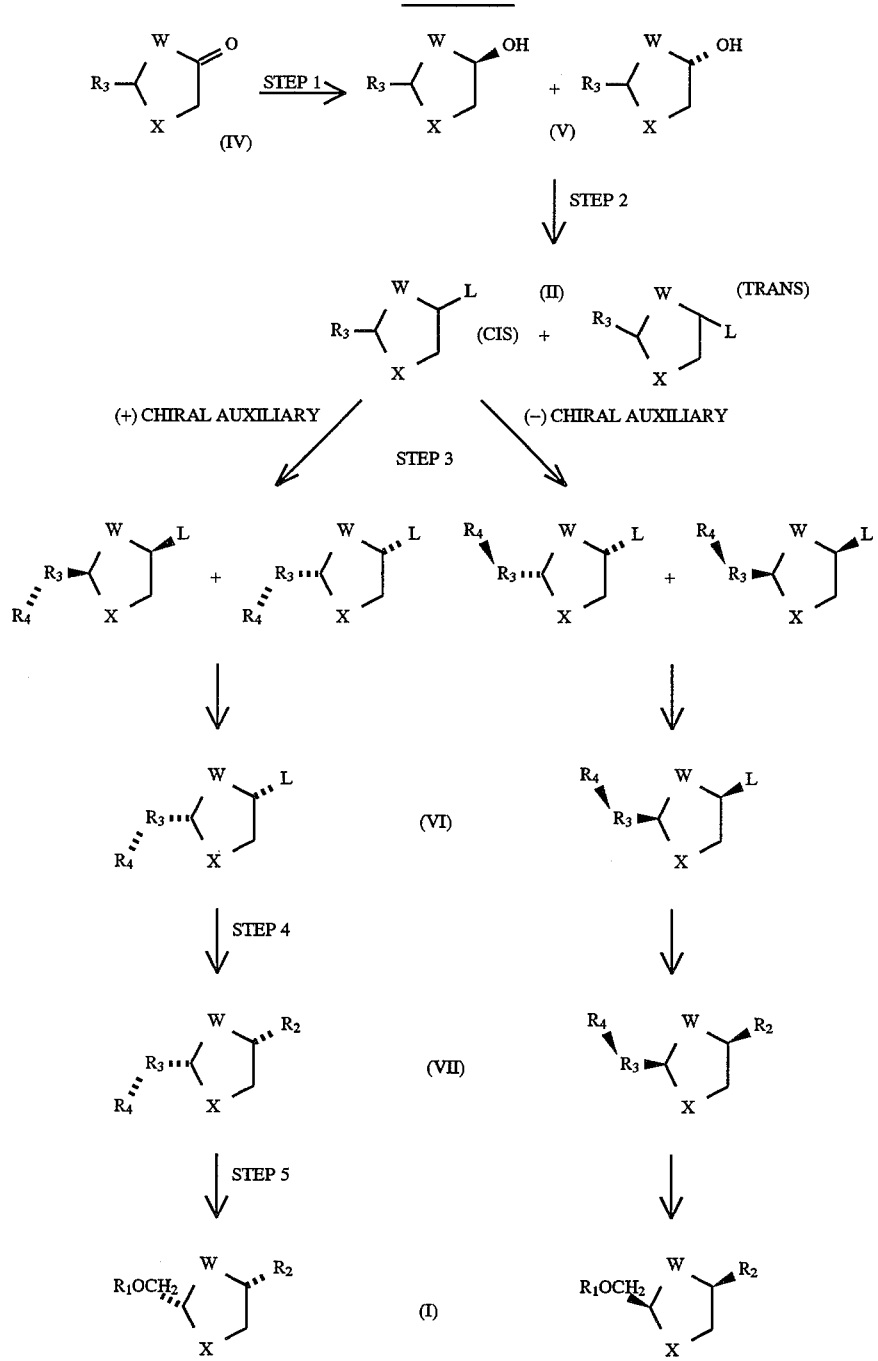
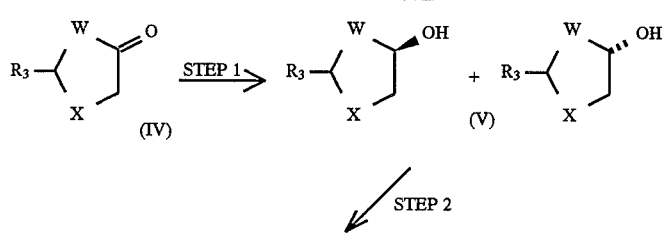

-continued
SCHEME IB

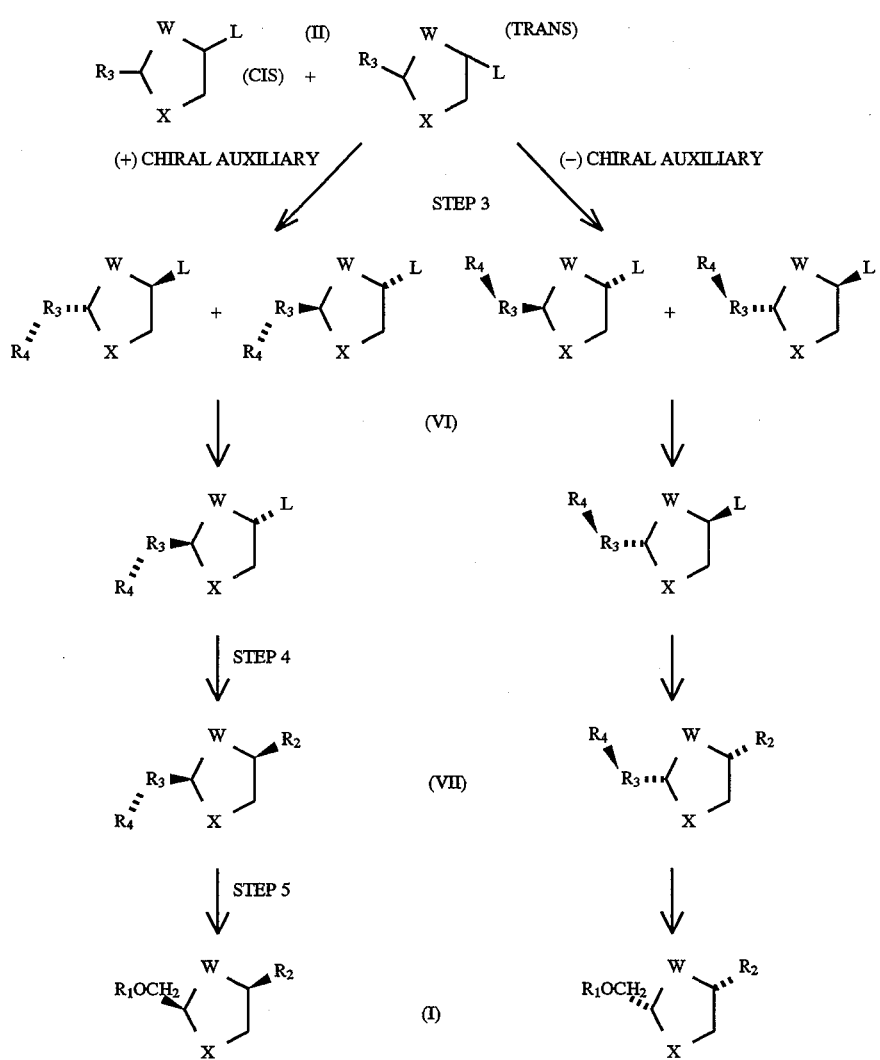

The various steps as illustrated in Schemes 1A and 1B may be briefly described as follows:

Step 1: The starting carbonyl-sugar of formula (IV) can be prepared by any method known in the art. E.g., J. M. Mcintosh et al., "2-Mercaptoaldehyde Dimers and 2,5-Dihydrothiophenes from 1,3-oxathiolan-5-ones", Can. J. Chem., 61, pp. 1872–1875 (1983). The carbonyl group of this starting compound is reduced chemoselectively with a suitable reducing agent, such as disiamylborane to give the cis- and trans-isomers of formula (V). Ordinarily, less cis-isomer is produced than trans.

Step 2: The hydroxyl group in the intermediate of formula (V) is readily converted to a leaving group by any method known in the art (e.g., T. W. Greene Protective Groups In Organic Synthesis, pp. 50–72, John Wiley & Sons, New York (1981)) to give the novel intermediates of formula (II).

This anomeric mixture is then separated by fractional crystallization into the two configurational isomers. The solvent may be adjusted to select for either the cis- or trans-isomer. D. J. Pasto and C. R. Johnson, Organic Structure Determination, pp. 7–10, Prentice-Hall, Inc., New Jersey (1969).

Step 3: Either the cis- (Scheme 1A) or trans-isomer (Scheme 1B) of formula (II) is chemically resolved using a chiral auxiliary ($R_4$). A suitable chiral auxiliary is one of high optical purity and where the mirror image is readily available, such as d- and l-menthol. The resulting diastereomers of formula (VI) are easily separated by fractional crystallization. Alternatively, either the cis- or the trans-isomer may be resolved enzymatically or by other methods known in the art. Jacques et al., Enantiomers, Racemates And Resolutions, pp. 251–369, John Wiley & Sons, New York (1981).

The optical purity of the diastereomer (VI, VII or I) can be determined by chiral HPLC methods, specific rotation measurements and NMR techniques. As a general rule, if the opposite enantiomer is desired, it may be obtained by using the mirror image of the chiral auxiliary initially employed. For example, if the chiral auxiliary d-menthol produces a (+)-enantiomer nucleoside, its mirror image, l-menthol, will produce the (−)-enantiomer.

Step 4: A previously silylated (or silylated in situ) purine or pyrimidine base or analogue or derivative thereof is then glycosylated with the resulting pure diastereomer in the presence of a Lewis acid of formula (III), such as iodotrimethylsilane (TMSI) or trimethylsilyl triflate (TMSOTf), to give a nucleoside of cis-configuration of formula (VII). This nucleoside is optically active and is substantially free of the corresponding trans-isomer (i.e., it contains less than 20%, preferably no more than 10% and more preferably no more than 5% of the trans-isomer).

The preferred silylating agent for pyrimidine bases are t-butyldimethylsilyl triflate 1,1,1,3,3,3 hexamethyldisilazane and trimethylsilyl triflate. It is believed that the bulky t-butyl group increases yields by weakening the interaction between the Lewis acid and silylated pyrimidine base.

The preferred method of mixing reagents in Step 4 is to first add the chiral auxiliary-sugar of formula (VI) to the silylated purine or pyrimidine base. The Lewis acid of formula (III) is then added to the mixture.

Step 5: The cis-nucleoside obtained in Step 4 may then be reduced with an appropriate reducing agent to remove the chiral auxiliary and give a specific stereoisomer of formula (I). The absolute configuration of this stereoisomer corresponds to that of the nucleoside intermediate of formula (VII). As shown in Scheme 1, either the cis- (Scheme 1A) or the trans-isomers (Scheme 1B) obtained in Step 2 will yield a cis end product.

Schemes 2A and 2B illustrate the application of the process of Schemes 1A and 1B to the synthesis of the enantiomers of cis-2-hydroxymethyl-5-(cytosin-1'-yl)-1,3-oxathiolanes. Although this process is illustrated using specific reagents and starting materials, it will be appreciated by one of skill in the art that suitable analogous reactants and starting materials may be used to prepare analogous compounds.

SCHEME 2A

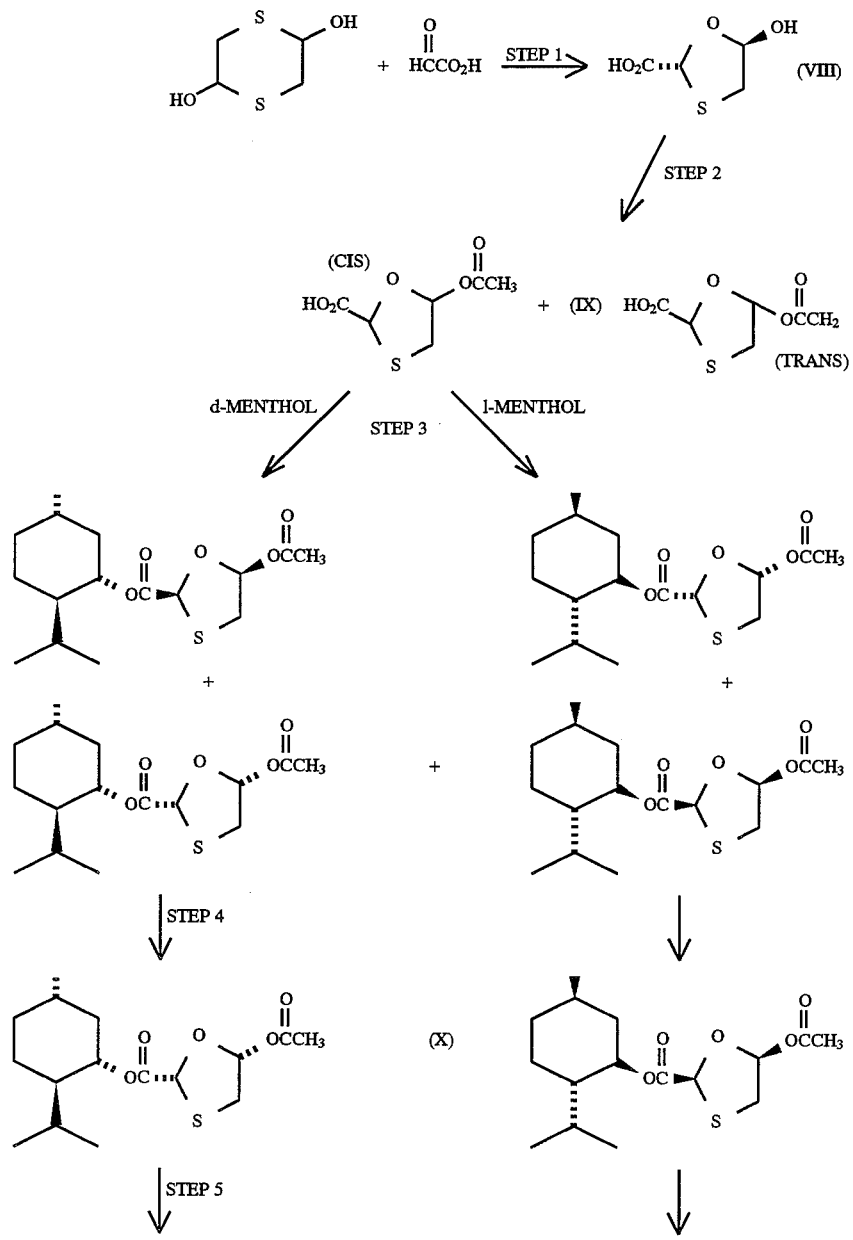

-continued
SCHEME 2A
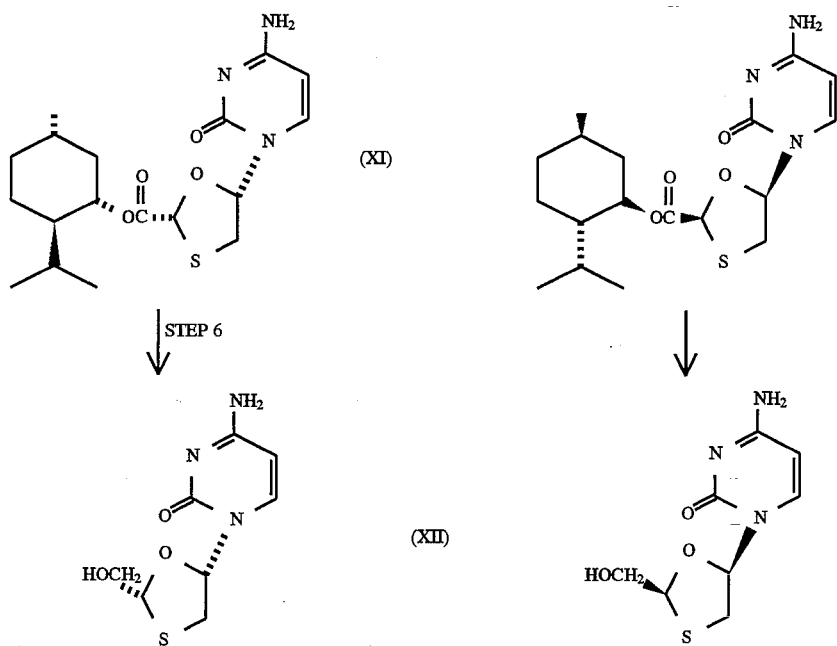
SCHEME 2B
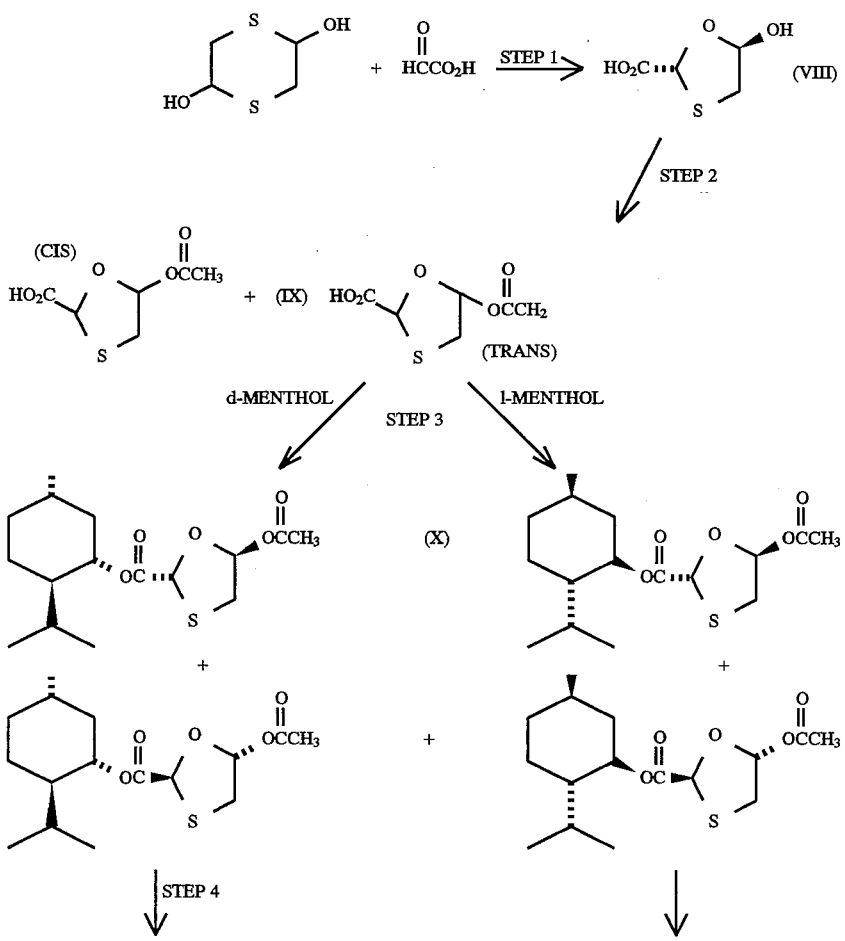

-continued
SCHEME 2B

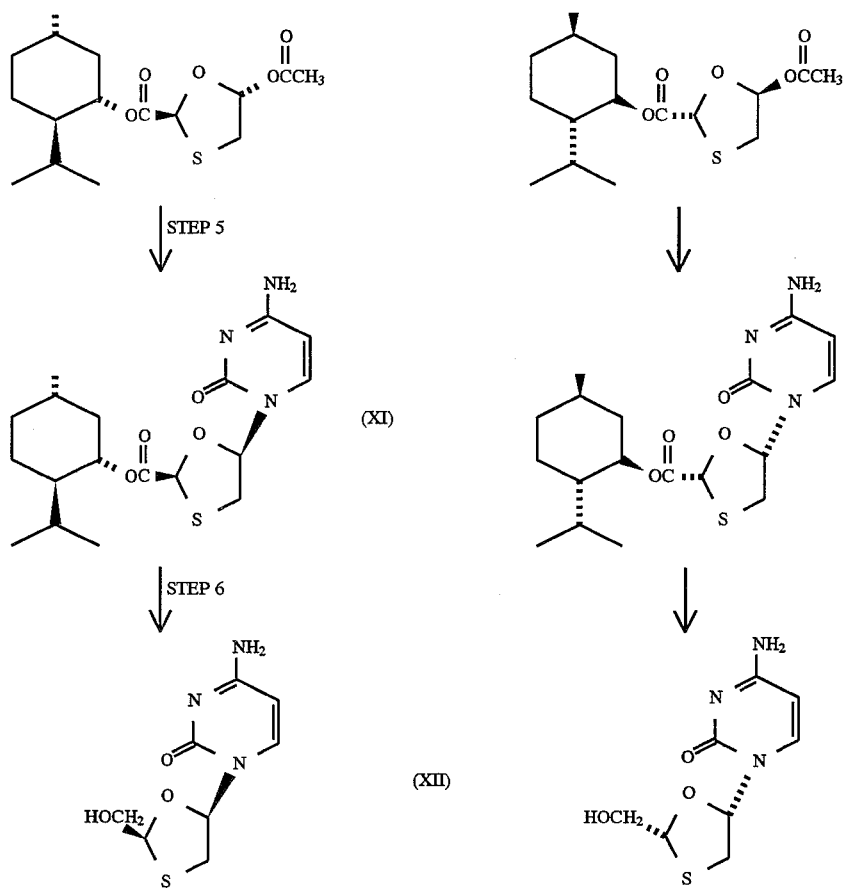

The various steps illustrated in Schemes 2A and 2B may be briefly described as follows:

Step 1: A mercaptoacetaldehyde monomer, preferably produced from a dimer, such as 2,5-dihydroxy-1,4-dithiane, in an appropriate solvent (preferably t-butylmethyl ether) is reacted with glyoxylic acid to give exclusively the trans-hydroxy acid of formula (VIII).

Step 2: The acid of formula (VIII) is reacted with an acid chloride, such as acetyl chloride in the presence of pyridine and an acylation catalyst, such as 4-dimethylaminopyridine, or preferably with an acid anhydride such as acetic anhydride in the presence of acetic acid and an acylation catalyst, such as sulfuric acid, to give a diastereomeric mixture of cis- and trans-acetoxy acids of formula (IX).

The racemic diastereomeric acid mixture obtained in Step 2 is fractionally crystallized using any combination of solvents (preferably benzene and ether) to give exclusively either the cis- or the trans-acetoxy acid of formula (IX) each as a racemic mixture.

Step 3: Either the cis- or the trans-acetoxy acid of formula (IX) is reacted with an appropriate chiral auxiliary preferably, 1-menthol or d-menthol, in a suitable organic solvent, such as dichloromethane, using an activating agent, such as dicyclohexylcarbodiimide, and an esterification catalyst, such as 4-dimethylaminopyridine, to give a diastereomeric mixture of the cis- or trans-esters respectively.

Alternatively, the compound of formula (IX) may be converted to an acid chloride by any means known in the art, such as with oxalyl chloride in an appropriate solvent, e.g., dichloromethane or $N_1N$-dimehylformamide. The acid chloride is then reacted with a chiral auxiliary in a suitable organic solvent using an esterification catalyst.

Step 4: The above diastereomeric mixture of either the cis- or the trans-esters is fractionally crystallized using any combination of solvents (preferably ether and petroleum ether (40°–60° C.)) preferably at low temperature to give exclusively the cis- or the trans-acetoxy menthyl ester of formula (X), respectively.

Step 5: Either the cis- or the trans-acetoxy compound of formula (X) is reacted with cytosine or other purine or pyrimidine base or analogue thereof. The purine or pyrimidine base or analogue is preferably previously silylated with hexamethyldisilazane or more preferably silylated in situ with t-butyldimethylsilyl triflate in a compatible organic solvent, such as dichloromethane containing a hindered base preferably 2,4,6-collidine. A Lewis acid of formula (III), preferably iodotrimethylsilane or trimethylsilyl triflate, is then added to give the cis-compound of formula (XI) in a highly diastereoselective manner.

Step 6: The optically active cis-nucleoside of formula (XI) is reduced stereospecifically with a reducing agent preferably lithium triethylborohydride or more preferably lithium aluminum hydride in an appropriate solvent such as tetrahydrofuran or diethyl ether to give the compound of formula (XII) and menthol.

A second process for the diastereoselective synthesis of compounds of formula (I) is illustrated by Schemes 3A and 3B and 4A and 4B. In the process of Schemes 3A and 3B carbonyl-sugar with an $R_3$ substituent at $C_4'$ is reacted with a chiral auxiliary ($R_4$) to give a diastereomeric mixture of two optically active chiral auxiliary sugars. The actual diastereomer produced depends on whether the (+) or (−) chiral auxiliary is used. This optically active mixture may be chemoselectively reduced and the resulting hydroxyl group converted to a leaving group to afford a diastereomeric mixture of four chiral auxiliary-sugars, two in the cis-configuration and two in the trans-configuration (Scheme 3B). Subsequent fractional crystallization gives a single diastereomer.

Alternatively, the optically active mixture of chiral auxiliary-sugars may first by separated by chromatography or fractional crystallization and then reduced and the resulting hydroxyl group converted to a leaving group (Scheme 3A). Subsequent fractional crystallization yields any desired diastereomer. The solvent may be adjusted to select for either the cis- or the trans-isomer. Each isolated optically active diastereomer-may be carried on further to compounds of formula (I) in a manner analogous to that described in Schemes 1 and 2.

Schemes 3A and 3B depict the second process of this invention as applied to any 1,3-oxathiolane, 2,4-dioxolane or 1,3-dithiolane.

SCHEME 3A

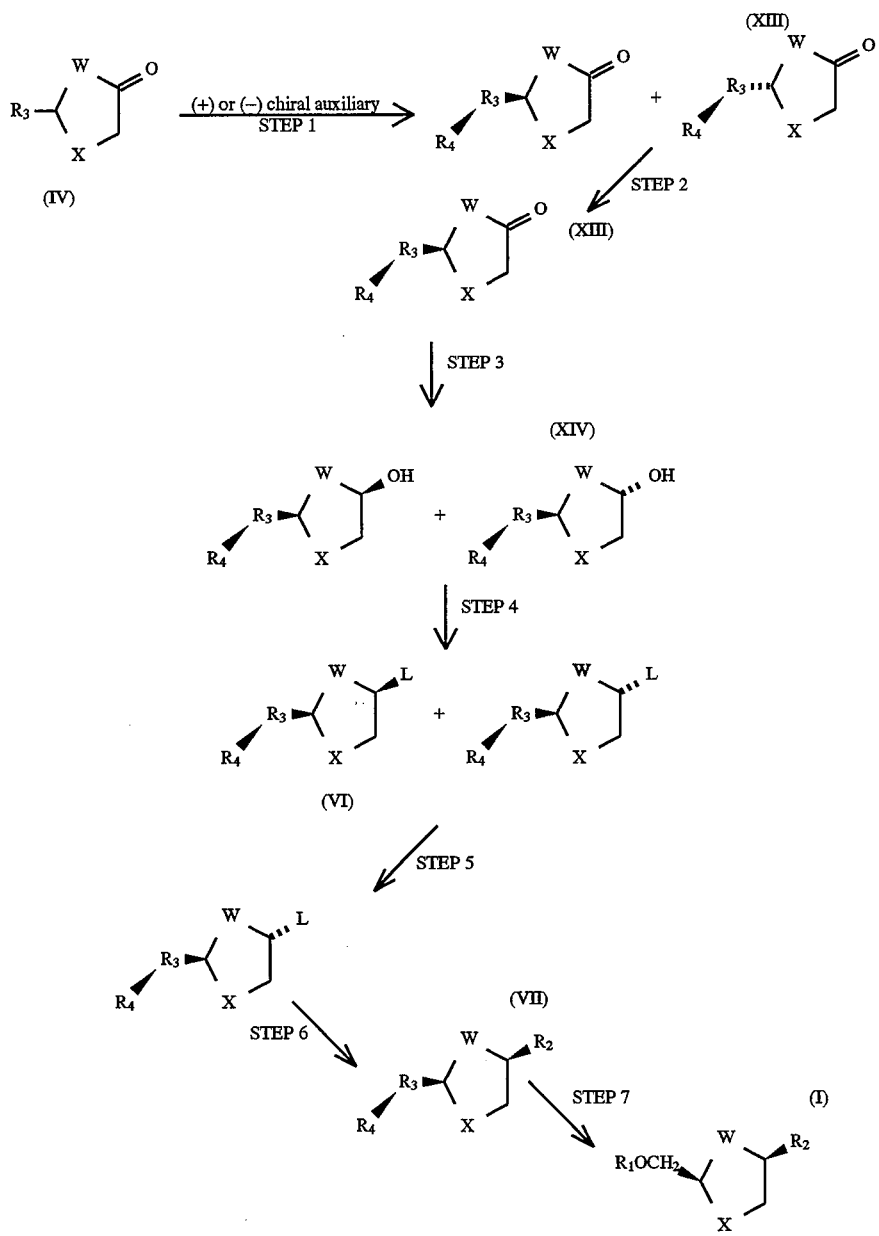

SCHEME 3B

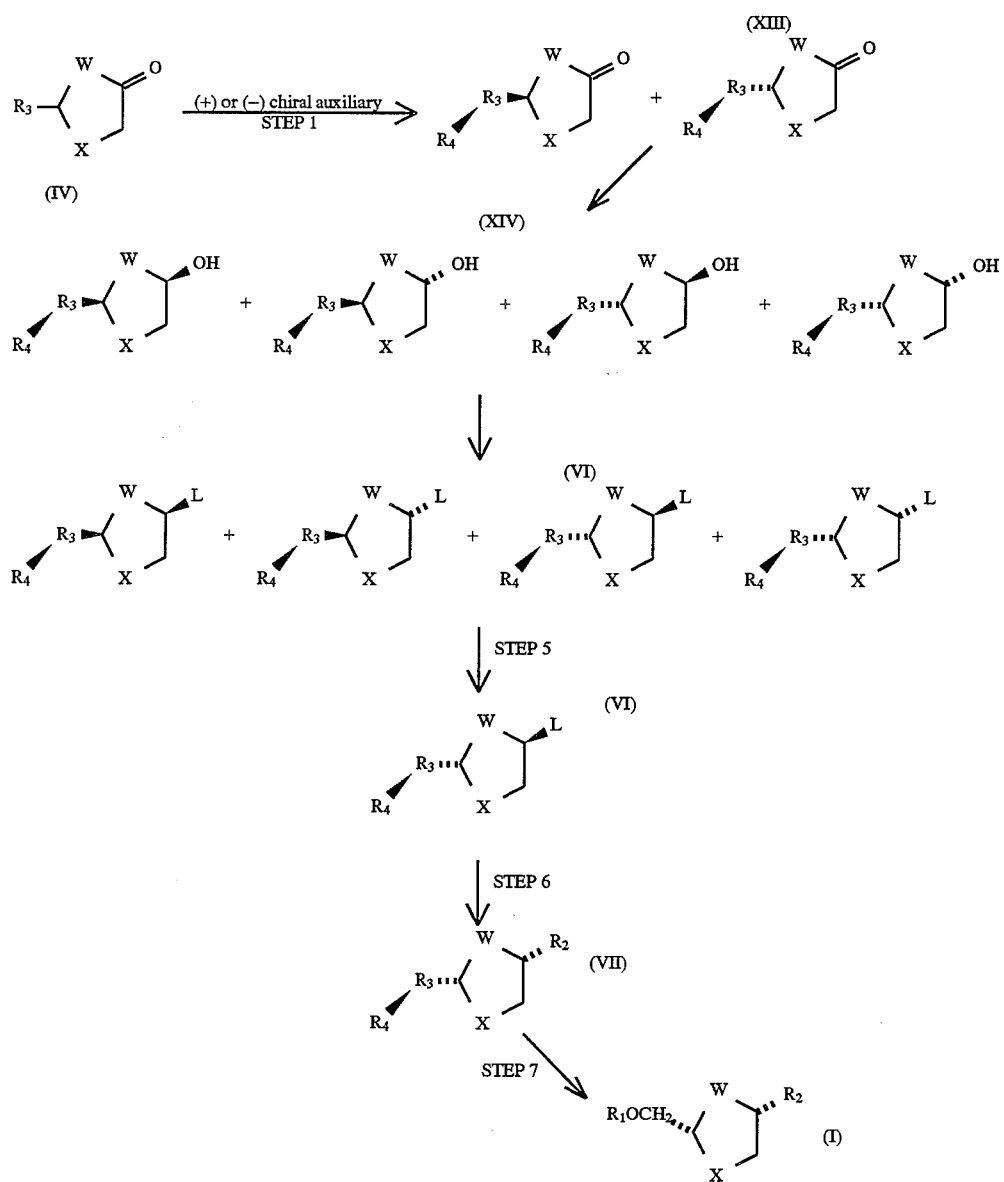

The various steps involved in the synthesis of the nucleosides of formula (I) as depicted in Schemes 3A may be briefly described as follows:

Step 1: The starting material of formula (IV), prepared by any method known in the art, is reacted with a chiral auxiliary (see, e.g., T. W. Greene, "Protective Groups in Organic Synthesis", John Wiley and Sons, New York (1981) to yield a mixture of two diastereomers of formula (XIII). The particular mixture produced will depend on which chiral auxiliary (+ or −) is used.

Step 2: The mixture of two diastereomers of formula (XIII) is separated by fractional crystallization or chromatography to yield one diastereomer of formula (XIII).

Step 3: The single isomer of formula (XIII) is chemoselectively reduced by a suitable reducing agent, such as disiamylborane to give a mixture of two diastereomers of formula (XIV).

Step 4: The hydroxyl groups of the two diastereomers of formula (XIV) are converted to leaving groups by any method known in the art to give a mixture of two diastereomers of formula (VI).

Step 5: Either the cis- or trans-isomer is separated out of the mixture of two diastereomers of formula (VI), as obtained in Step 4, by fractional crystallization or chromatography. The solvent may be adjusted to select for the cis- or trans-isomer.

Step 6: The single diastereomer of formula (VI) is reacted with previously silylated (or silylated in situ) purine or pyrimidine base or analogue or derivative. Then, addition of a Lewis acid of formula (III), such as iodotrimethylsilane (TMSI) or trimethylsilyl triflate (TMSOTf) yields a nucleoside of cis-configuration of formula (VII). This nucleoside is substantially free of the corresponding trans-isomer.

Step 7: The optically active cis-nucleoside of formula (VII) is reduced stereospecifically with a reducing agent preferably lithium triethylborohydride or more preferably lithium aluminum hydride in an appropriate solvent such as tetrahydrofuran or diethyl ether to give the compound of formula (I) and menthol.

Alternatively, as shown in Scheme 3B, the mixture of diastereomers of formula (XIII) is chemoselectively reduced with a suitable reducing agent, such as disiamylborane to give a mixture of four diastereomers of formula (XIV). The hydroxyl groups in this mixture of four diastereomers of formula (XIV) are converted to leaving groups any method in the art to afford a mixture of four diastereomers of formula (VI). Either a cis- or a trans-isomer of formula (VI) is separated out of the mixture of four diastereomers of formula (VI) by fractional crystallization or chromatography. The solvent may be adjusted to select for a cis- or trans-isomer. The single diastereomer of formula (VI) is reacted with previously silylated (or silylated in situ) purine or pyrimidine base or analogue or derivative. Then, addition of a Lewis acid of formula (III), such as iodotrimethylsilane (TMSI) or trimethylsilyl triflate (TMSOTf) affords a nucleoside of cis- configuration of formula (VII) which is reduced with an appropriate reducing agent to give a specific stereoisomer of formula (I).

Schemes 4A and 4B illustrate the application of the process of Scheme 3 to the synthesis of the enantiomers of cis-2-hydroxymethyl-5-(cytosin-1'-yl)-1,3-oxathiolanes. Although this process is illustrated using specific reagents and starting materials, it will be appreciated by one of skill in the art that suitable analogous reactants and starting materials may be used to prepare analogous compounds.

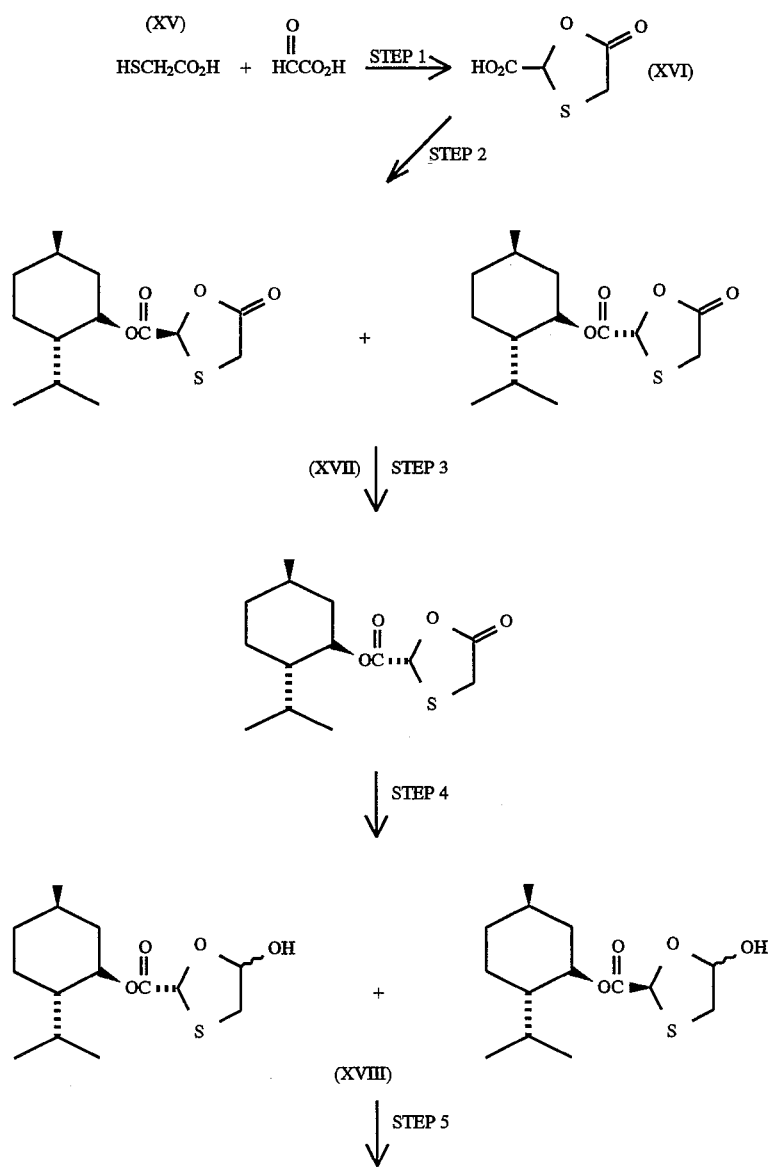

SCHEME 4A

-continued
SCHEME 4A
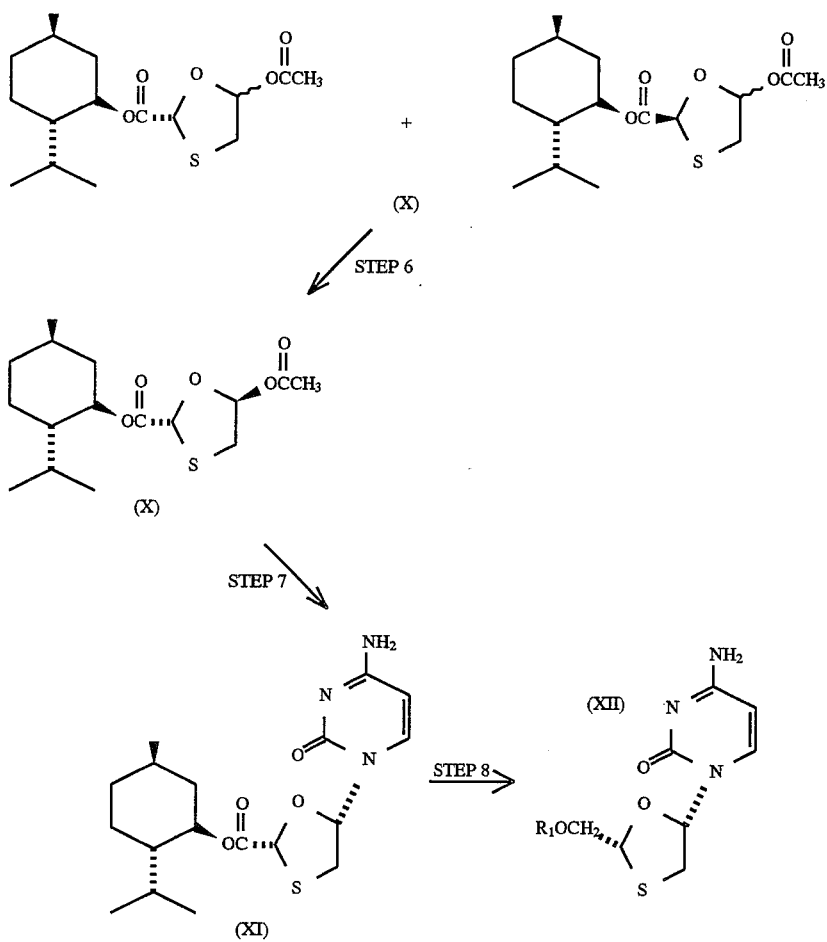
SCHEME 4B
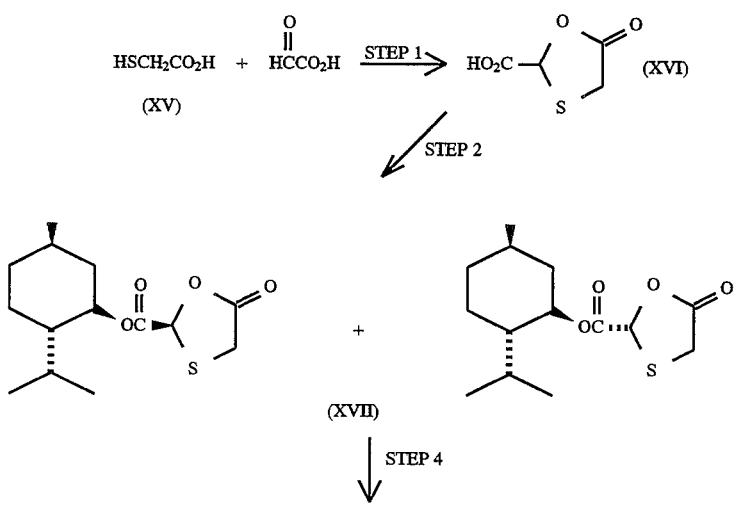

-continued
SCHEME 4B

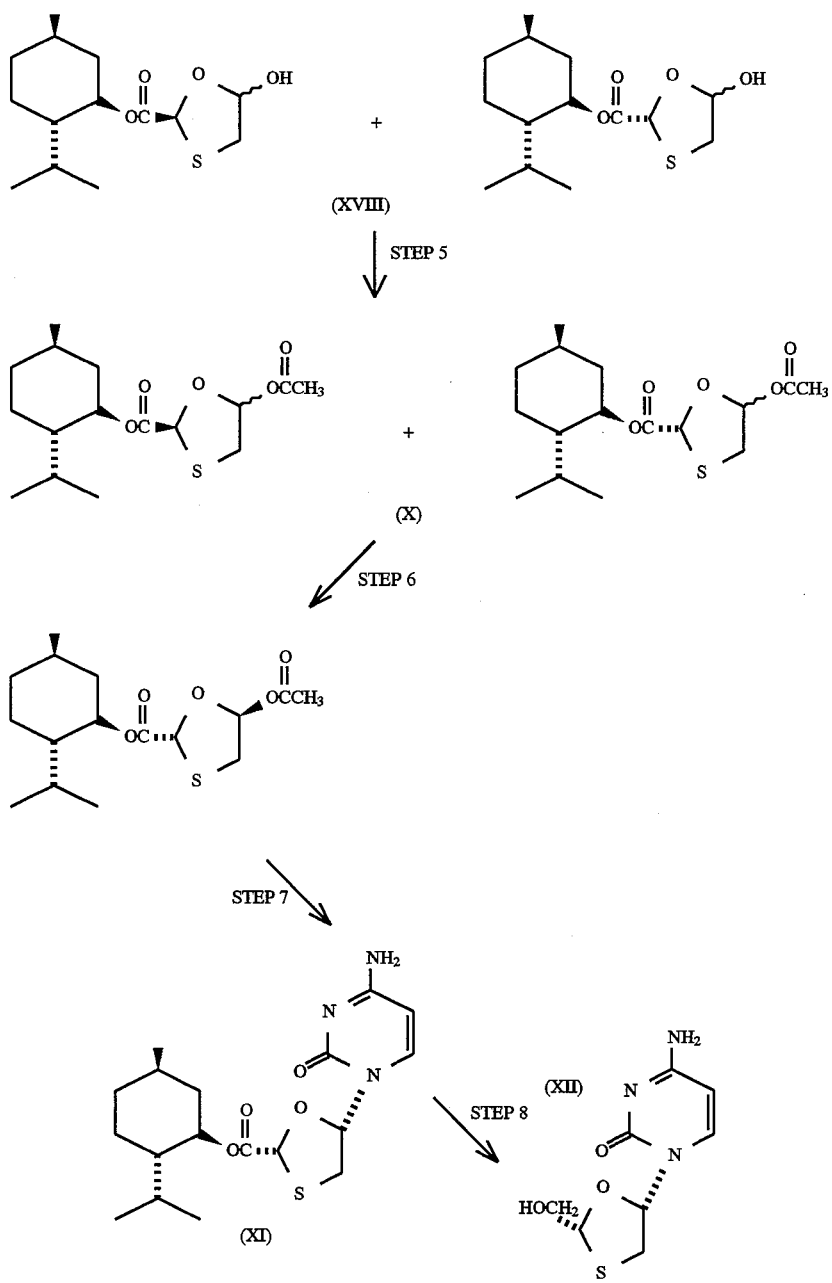

The various steps involved in the synthesis of the nucleosides of formula (I) as depicted in Scheme 4 may be briefly described as follows:

Step 1: The known mercaptoacetic acid of formula (XV) is reacted with an appropriate aldehyde of formula $R_3CHO$, wherein $R_3$ is preferably an alkoxy carbonyl, such as menthyl glyoxylate and more preferably a carboxyl group, such as glyoxylic acid (see e.g., J. M. Mcintosh et al., "2-Mercaptoaldehyde Dimers and 2,5-Dihydrothiophenes from 1,3-oxathiolan-5-ones", *Can. J. Chem.*, 61, pp. 1872–1875 (1983)) in a compatible organic solvent, such as toluene, to give the intermediate of formula (XVI).

Step 2: The compound of formula (XVI) is reacted with an appropriate chiral auxiliary, preferably 1-menthol or d-menthol in a compatible organic solvent, such as dichloromethane, using an activating agent, such as dicyclohexylcarbodiimide, and an esterification catalyst, such as 4-dimethylaminopyridine, to give the compounds of formula (XVII).

Step 3: The diastereomeric compounds of formula (XVII) are preferably separated by fractional crystallization (Scheme 4A), but may be carried on further without separation (Scheme4B).

Step 4: The compounds of formula (XVII) are reduced with an appropriate reducing agent such as disiamylborane in a compatible organic solvent, such as tetrahydrofuran (A. Pelter et al., "Borane Reagents", Academic Press, p. 426 (1988)), to give the compounds of formula (XVIII).

Step 5: The compounds of formula (XVIII) are reacted with an acid chloride or acid anhydride, such as acetic anhydride, in the presence of pyridine and an acylation catalyst, such as 4-dimethylaminopyridine, to give the compounds of formula (X).

Step 6: The diastereomeric compounds of formula (X), if not already separated (Scheme 4A), are now separated preferably by fractional crystallization (Scheme 4B) to give either the cis- or the trans-acetoxy compound of formula (X).

Step 7: Either the cis- or the trans-acetoxy compound of formula (X) is reacted with cytosine or other purine or pyrimidine base or analogue thereof. The purine or pyrimidine base or analogue is preferably previously silylated with hexamethyldisilazane or more preferably silylated in situ with t-butyldimethylsilyl triflate in a compatible organic solvent, such as dichloromethane containing a hindered base preferably 2,4,6-collidine. A Lewis acid, preferably one derived from the compounds of formula (III), more preferably iodotrimethylsilane or trimethylsilyl triflate, is then added to give the cis compound of formula (XI) in a highly diastereoselective manner.

Step 8: The optically active cis-nucleoside of formula (XI) is reduced stereospecifically with a reducing agent, preferably lithium triethylborohydride, or more preferably, lithium aluminum hydride, in an appropriate solvent, such as tetrahydrofuran or diethyl ether, to give the compound of formula (XII).

In the diastereoselective processes of this invention, the following intermediates are of particular importance:

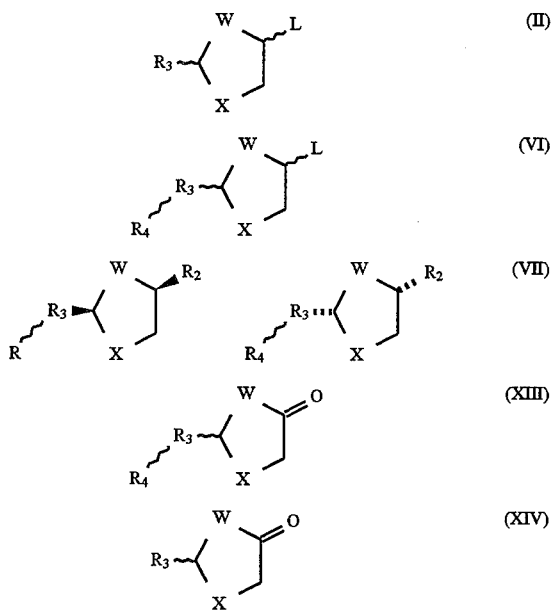

wherein $R_3$, $R_4$ and L are as defined above;
trans-5-hydroxyoxathiolane-2-carboxylic acid;
(1'R,2'S,5'R)-menthyl-1,3-oxathiolan-5-one-2S-carboxylate;
(1'R,2'S,5'R)-menthyl-1,3-oxathiolan-5-one-2R-carboxylate;
(1'R,2'S,5'R)-menthyl-5S-hydroxy-1,3-oxathiolane-2S-carboxylate;
(1'R,2'S,5'R)-menthyl-5R-hydroxy-1,3-oxathiolane-2R-carboxylate;
(1'R,2'S,5'R)-menthyl-5S-hydroxy-1,3-oxathiolane-2R-carboxylate;
(1'R,2'S,5'R)-menthyl-5R-hydroxy-1,3-oxathiolane-2S-carboxylate;
(1'R,2'S,5'R)-menthyl-5S-acetoxy-1,3-oxathiolane-2S-carboxylate;
(1'R,2'S,5'R)-menthyl-5R-acetoxy-1,3-oxathiolane-2R-carboxylate; (1'R, 2'S,5'R)-menthyl-5S-acetoxy-1,3-oxathiolane-2R-carboxylate;
(1'R,2'S,5'R)-menthyl-5R-acetoxy-1,3-oxathiolane-2S-carboxylate;
(1'S,2'R,5'S)-menthyl-5R-acetoxy-1,3-oxathiolane-2S-carboxylate;
(1'S,2'R,5'S)-menthyl-5S-acetoxy-1,3-oxathiolane-2R-carboxylate;
(1'S,2'R,5'S)-menthyl-5R-acetoxy-1,3-oxathiolane-2R-carboxylate;
(1,S,2'R,5'S)-menthyl-5S-acetoxy-1,3-oxathiolane-2S-carboxylate;
(1,R,2'S,5'R)-menthyl-5S-(cytosin-1"-yl)-1,3-oxathiolane-2R-carboxylate;
(1,S,2'R, 5'S)-menthyl-5S-(cytosin-1"-yl)-1,3-oxathiolane-2R-carboxylate;
(1,R,2'S,5'R)-menthyl-5R-(cytosin-1"-yl)-1,3-oxathiolane-2S-carboxylate;
(1,S,2'R, 5'S)-menthyl-5R-(cytosin-1"-yl)-1,3-oxathiolane-2S-carboxylate;
(1,R,2,S,5,R)-menthyl-5R-(5"-fluorocytosin-1"-yl)-1,3-oxathiolane-2S-carboxylate;
(1,S,2,R,5'S)-menthyl-5S-(5"-fluorocytosin-1"-yl)-1,3-oxathlolane-2R-carboxylate; (1,S,2,R,5'S)-menthyl-5S-(N-4"-acetylcytosin-1"-yl)-1,3-oxathiolane-2R-carboxylate;
(1,R,2,S,5'R)-menthyl-5S-(cytosin-1"-yl)-1,3-oxathiolane-2R-carboxylate;
(1,S,2,R,5'S)-menthyl-1,3-oxathiolane-2R-carboxylate;
(1,S,2,R,5'S)-menthyl-4R-hydroxy-1,3-oxathiolane-2R-carboxylate and (1'S,2'R,5'S)-menthyl-4S-hydroxy-1,3-oxathiolane-2R-carboxylate;
(1,S,2,R,5'S)-menthyl-4R-chloro-1,3-oxathiolane-2R-carboxylate and (1'S,2'R,5'S)-menthyl-4S-chloro-1,3-oxathiolane-2R-carboxylate;
cis-2(N-methyl-N-methoxyaminocarbonyl)-5-(uracil-1'-yl)-1,3-oxathiolane;
cis- and trans-2-benzoyl-5-acetoxy-1,3-oxathiolane;
cis-2-(1'-pyrrolidinocarbonyl)-5-acetoxy-1,3-oxathiolane;
cis-2-carbomethoxy-5-(5'-bromouracil-1'-yl)-1,3-oxathiolane;
cis-2-carboxyl-5-(uracil-1'-yl)-1,3-oxathiolane;
cis-2-(1'-pyrrolidinocarbonyl)-5-(uracil-1'-yl)-1,3-oxathiolane;
cis-2-benzoyl-5-(uracil-1'-yl)-1,3-oxathiolane;
cis- and trans-isopropyl-5-acetoxy-1,3-oxathiolane-2-carboxylate;
cis-isopropyl-5-(cytosin-1'-yl)-1,3-oxathiolane-2-carboxylate;
cis- and trans-t-butyl-5-acetoxy-1,3-oxathiolane-2-carboxylate;
cis-t-butyl-5-(cytosin-1'-yl)-1,3-oxathiolane-2-carboxylate;
cis- and trans-2-N,N-diethylaminocarbonyl-5-acetoxy-1,3-oxathiolane;
cis-2-N,N-diethylaminocarbonyl-5-(cytosin-1'-yl)-1,3-oxathiolane;
cis- and trans-2-carboethoxy-4-acetoxy-1,3-dioxolane;
cis- and trans-2-carboethoxy-4-(thymin-1'-yl)-1,3-dioxolane; and
cis- and trans-2-carboethoxy-4-(N-4'-acetylcytosin-1'-yl)-1,3-dioxolane.

The following examples illustrate the present invention in a manner of which it can be practiced but, as such, should not be construed as limitations upon the overall scope of the processes of this invention. Except where specifically noted, all $[\alpha]_D$ measurements were recorded at ambient temperature.

EXAMPLE 1

1,3-OXATHIOLAN-5-ONE-2-CARBOXYLIC ACID

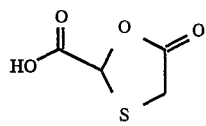
(XVI)

Toluene (700 mL), mercaptoacetic acid (38 mL, 50.03 g, 0.543 mol), and p-toluenesulfonic acid (1.0 g) were added to a solution of glyoxylic acid monohydrate (50.0 g, 0.543 mol) in 200 mL of THF in a 2 L round bottom flask equipped with a Dean-Stark trap and condenser. The resultant reaction mixture was refluxed for 3 hours until 24.0 mL of $H_2O$ was azeotropically removed. The reaction mixture was cooled, followed by removal of solvent under reduced pressure to yield an off-white solid. This material was purified by recrystallization (hexanes-EtOAc) to give 60.0 g of the product as a crystalline white solid: m.p. 140°–143° C.; $^1H$ NMR (DMSO) δ3.84 (g, 2H, JAB=16.7 Hz), 6.00 (s, 1H).

EXAMPLE 2

TRANS-5-HYDROXYOXATHIOLANE-2-CARBOXYLIC ACID

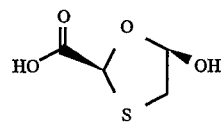
(VIII)

A suspension of dithian-1,4-diol (82.70 g, 0.54 mol) and glyoxylic acid monohydrate (100.0 g, 1.09 mol) in tert-butyl methyl ether (1.1 L) was stirred under a blanket of nitrogen and heated to reflux under Dean and Stark conditions. The reflux was continued for 8 hours during which time 15.3 mL (0.85 mol) of water was collected. The slightly turbid mixture was filtered, and the solvent was distilled at atmospheric pressure until a volume of 600 mL remained. Cyclohexane (340 mL) was added and the solution was cooled to 5° C., seeded, and allowed to stir and crystallize. The suspension was stirred at 0°–5° C. for 2 hours. The product was isolated by filtration, washed with 100 mL of tert-butyl methyl ether-cyclohexane (2:1), and was dried overnight in vacuo at room temperature (94.44 g): m.p. 94.5° C.; $^1HNMR$ (DMSO) δ2.85 (dd, 1H, J=2.4, 10.5 Hz), 3.13 (dd, 1H, J=4.3, 10.5 Hz), 5.47 (s, 1H), 5.84 (brs, 1H), 6.95 (d, 1H, J=4.7 Hz).

EXAMPLE 3

TRANS-5-ACETOXY-1,3-OXATHIOLANE-2-CARBOXYLIC-ACID

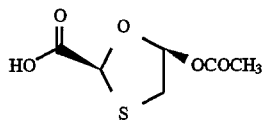
(IX)

One drop of concentrated $H_2SO_4$ was added to a thoroughly stirred solution of trans-5-hydroxyoxathiolane-2-carboxylic acid (7.0 g, 46.7 mmol) in glacial acetic acid (40 mL) and acetic anhydride (15 mL, 15.9 mmol) at ambient temperature. The resultant clear solution was stirred for I hour and then poured onto crushed ice and brine (20 mL). This mixture was extracted with $CH_2Cl_2$ (100 mL) and the combined extract was dried over anhydrous magnesium sulfate. The solvent was removed under reduced pressure to give 8.5 g (95%) of a light yellow syrup which consisted of trans- and cis-5-acetoxy-1,3-oxathiolane-2-carboxylic acid in a 2:1 ratio. The mixture was dissolved in benzene (20 mL) and was left standing overnight during which white crystals were formed. A small amount of ether was added and the solid was collected by filtration and washed with more ether to give 2 g (22%) of trans-5-acetoxy-1,3-oxathiolane-2-carboxylic acid: m.p. 111.3° C.; $^1H$ NMR (DMSO) δ2.03 (s, 3H), 3.21 (d, 1H, J=12 Hz), 3.32 (dd, 1H, J=3, 12 Hz), 5.65 (s, 1H), 6.65 (d, 1H, J=4 Hz); $^{13}C$ NMR (DMSO) δ20.91, 36.51, 78.86, 99.15, 169.36, 170.04.

EXAMPLE 4

CIS-5-ACETOXY-1,3-OXATHIOLANE-2-CARBOXYLIC ACID

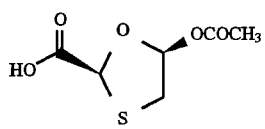
(IX)

The filtrate obtained from Example 3 was concentrated under reduced pressure and redissolved in ether. This solution was kept at room temperature and cis-5-acetoxy-1,3-oxathiolane-2-carboxylic acid slowly crystallized out as a white solid (2.1 g, 23%): m.p. 111.7° C.; $^1H$ NMR (DMSO) δ1.96 (s, 3H), 3.25–3.33 (m, 2H), 5.74 (S, 1H), 6.69 (d, 1H, J=3 Hz); $^{13}C$ NMR (DMSO) δ21.0, 37.16, 79.57, 98.58, 169.36, 170.69.

EXAMPLE 5

(1,R,2,S,5,R)-MENTHYL-1,3-OXATHIOLAN-5-ONE-2S-CARBOXYLATE AND (1'R,2'S,5'R)-MENTHYL-1,3-OXATHIOLAN-5-ONE-2R-CARBOXYLATE

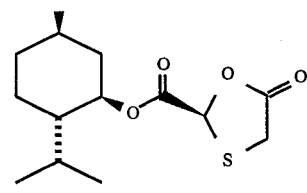

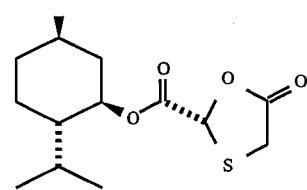
(XVII)

Oxalyl chloride (11 mL, 123.6 mmol) was added through a dropping funnel over a period of 30 minutes to a stirred solution of 1,3-oxathiolan-5-one-2 -carboxylic acid (12.2 g, 82.4 mmol) in anhydrous THF (20 ml) and $CH_2Cl_2$ (40mL) at room temperature under an argon atmosphere. The resultant solution was heated at 65° C. for 30 minutes and then was concentrated in vacuo to give an oily product (11.6 g, 90%). The crude acid chloride obtained was redissolved in dry $CH_2Cl_2$ (40 mL) and cooled at 0° C. (1R,2S,5R)-menthol (12.8 g, 82.4 mmol) dissolved in $CH_2Cl_2$ (25 mL) was slowly added to this cooled solution. The resultant solution was stirred at room temperature overnight. The reaction mixture was diluted with $CH_2Cl_2$ (200 mL) and washed with water, saturated aqueous $NaHCO_3$ solution, brine, and then was dried over anhydrous $Na_2SO_4$. The solvent was removed and the crude product thus obtained was filtered through a short silica column (100 g, Merck)

eluted with EtOAc-hexanes. Concentration of the appropriate fractions gave a 1:1 mixture of (1'R,2'S,5'R)-menthyl-1,3-oxathiolan-5-one-2S-carboxylate and (1,R,2'S,5'R)-menthyl-1,3-oxathiolan-5-one-2R-carboxylate (20 g, 84.7% overall) as a viscous oil: $^1$H NMR (CDCl$_3$) δ0.77 (3H), 0.91 (6H), 1.00–1.15 (2H), 1.40–2.10 (6H), 3.56 (1H), 3.82 (1H), 4.80 (1H), 5.62 (1H); $^{13}$C NMR δ16.7, 21.2, 21.3, 22.5, 23.80, 23.84, 26.7, 26.8, 30.6, 31.91, 31.94, 34.57, 40.6, 41.07, 47.5, 47.6, 74.1, 74.2, 77.7, 168.1, 172.8.

The above mixture (20 g) was dissolved in a minimum amount of pentans-petroleum ether (40°–60° C.) (1:2, 30 mL). The resultant solution was cooled at −70° C. for 10 minutes and the crystalline compound that was formed was quickly collected by filtration and washed with more cold petroleum ether (10 mL). This crystalline compound, isolated in 12.5% yield, was found to consist of one isomer as indicated by $^1$HNMR and $^{13}$C NMR spectroscopy: m.p. 78.5°; [α]$_D$+31.7° (c, 0.984, CHCl$_3$); $^1$H NMR (CDCl$_3$) δ0.77 (3H), 0.91 (6H), 1.00–1.15 (2H), 1.40–2.10 (6H), 3.56 (1H), 3.82 (1H), 4.79 (1H), 5.62 (1H); $^{13}$C NMR (CDCl$_3$) δ16.7, 21.2, 22.5, 23.8, 26.7, 30.0, 32.0, 34.6, 41.1, 47.6, 77.7, 168.1, 172.9.

EXAMPLE 6

(1'R,2'S,5'R)-MENTHYL-5S-HYDROXY-1,3-OXATHIOLANE-2S-CARBOXYLATE, (1'R,2'S,5'R)-MENTHYL-5R-HYDROXY-1,3-OXATHIOLANE-2R-CARBOXYLATE, (1'R,2'S,5'R)-MENTHYL-5S-HYDROXY-1,3-OXATHIOLANE-2R-CARBOXYLATE, (1'R,2'S,5'R)-MENTHYL-5R-HYDROXY-1,3-OXATHIOLANE-2S-CARBOXYLATE

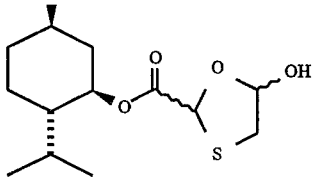

(XVIII)

A freshly prepared solution of disiamylborane (13.4 mmol, 0.5M in THF) was added via canula to a stirred solution of a 1:1 mixture of the menthyl ester carboxylate of formula (XVII) (1.28 g, 4.47 mmol) in THF (10 mL) at 0° C. under an argon atmosphere. The resulting clear solution was stirred for 15 minutes at 0° C. and 18 hours at ambient temperature. The reaction was quenched with methanol (5 mL), concentrated, and diluted with methylene chloride (20 mL). The resultant solution was washed with brine (5×2 mL) and dried over anhydrous magnesium sulfate. Removal of the solvent gave a clear oil. Subjecting this material to silica gel column chromatography (EtOAc-hexanes, 1:2, V/V) gave 0.65 g (50%) of the expected lactols in four diastereomeric forms: $^1$H NMR (CDCl$_3$) δ0.71–2.09 (m, 18H), 3.01–3.09 (m, 1H), 3.24–3.33 (m, 1H), 4.66–4.83 (m, 1H), 5.53–5.59 (m, 1H), 5.88–6.09 (m, 1H).

EXAMPLE 7

(1'R,2'S,5'R)-MENTHYL-5S-ACETOXY-1,3-OXATHIOLANE-2S-CARBOXYLATE, (1'R,2'S,5'R)-MENTHYL-5R-ACETOXY-1,3-OXATHIOLANE-2R-CARBOXYLATE, (1'R,2'S,5'R)-MENTHYL-5S-ACETOXY-1,3-OXATHIOLANE-2R-CARBOXYLATE, (1'R, 2'S,5'R)-MENTHYL-5R-ACETOXY-1,3-OXATHIOLANE-2S-CARBOXYLATE

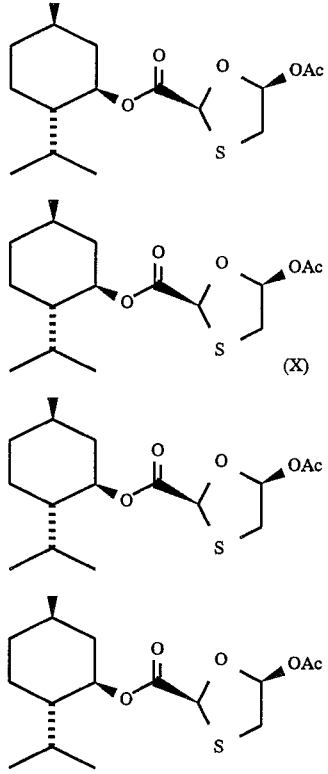

(X)

The four title compounds were prepared as a mixture by the following two methods.

Method A

Lactols of formula (XVIII) (0.65 g, 2.25 mmol) were dissolved in anhydrous pyridine (1.5 mL) and methylene chloride (5 mL). Acetyl chloride (0.5 mL, 7.0 mmol) was slowly added to this solution at 0° C. The resulting white suspension was stirred at ambient temperature for 3 hours. The reaction was then quenched with saturated aqueous ammonium chloride solution (1 mL). The mixture was extracted with methylene chloride (5×2 mL) and the combined extract was concentrated to give a brown gummy material. This material was subjected to column chromatography (EtOAc-hexane, 1:3 V/V) to provide 0.3 g of the four acetates as a light yellow oil: $^1$H NMR (CDCl$_3$) δ0.75 (d, 6H, J=7 Hz), 0.78 (d, 6H, J=7 Hz), 0.88–0.94 (m, 24H), 0.97–2.03 (m, 36M), 2.10 (s, 9H), 2.13 (s, 3H), 3.15 (d, 2H, J=12 Hz), 3.23–3.30 (m, 4H), 3.42 (dd, 1H, J=4, 12 Hz), 3.44 (dd, 1H, J=4, 12 Hz), 4.65–4.75 (m, 4H), 5.61 (s, 1H), 5.62 (s, 1H), 5.63 (s, 1H), 5.64 (s, 1H), 6.64 (m, 4H).

Method B

A solution of dicyclohexyl-carbodiimide (21.86 g, 0.106 mol) in dichloromethane (100 mL) was added to a 500 mL round bottom flask containing a solution of trans- and cis-5-acetoxy-1,3-oxathiolane-2-carboxylic acid (X) (18.5 g, 0.096 mol), (1R,2S,5R)-(−)-menthol (16.5 g, 0.106 mol), and 4-dimethyl-aminopyridine (1.17 g, 9.63 mmol) in dichloromethane (200 mL) at 0° C. The resulting thick white slurry was stirred at room temperature for 3 hours at which time methanol (4.0 mL) and glacial acetic acid (2.0 mL) were added. After stirring for 10 minutes, the reaction mixture was diluted with hexanes (200 mL) and filtered through Celite. Subsequent removal of the solvent provided 32.5 g of the crude product. This substance was redissolved in hexanes (100 mL), filtered through Celite and concentrated to yield 30.5 g of material which was further purified by column chromatography (eluent: 100% hexanes to 5% EtOAc-hexanes) to give 5.5 g of a mixture (ca. 1:1) of (1'R,2'S,5'R)-menthyl-5R-acetoxy-1,3-oxathiolane-2S-carboxylate and (1,R,2,S,5'R)-menthyl-5S-acetoxy-1,3-oxathiolane-2R-carboxylate; 10.28 g of a material which contained mainly the above two diastereomers along with (1,R,2,S,5,R)-menthyl-5S-acetoxy-1,3-oxathiolane-2S-carboxylate and (1,R,2'S,5'R)-menthyl-5R-acetoxy-1,3-oxathiolane-2R-carboxylate; 7.6 g of a random mixture of the above four diastereomers; and 2.2 g of a mixture (ca. 1:1) of (1'R,2'S,5'R)-menthyl-5S-acetoxy-1,3-oxathiolane-2S-carboxylate and (1'R,2'S,5'R)-menthyl-5R-acetoxy-1,3-oxathiolane-2R-carboxylate.

EXAMPLE 8

(1'R,2,S,5,R)-MENTHYL-5R-ACETOXY-1,3-OXATHIOLANE-2R-CARBOXYLATE

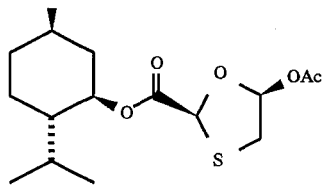

(X)

(1'R,2'S,5'R)-Menthyl-5R-acetoxy-1,3-oxathiolane-2R-carboxylate was prepared by the following three methods.
Method A A mixture of (1'R,2'S,5'R)-menthyl-5S-acetoxy-1,3-oxathiolane-2S-carboxylate and (1'R,2'S,5'R)-menthyl-5R-acetoxy-1,3-oxathiolane-2R-carboxylate (5.5 g) obtained from Example 7 was dissolved in petroleum ether (40°–60° C.) containing a minimum amount of diethyl ether and cooled in a dry ice-acetone bath. The white solid precipitate was immediately collected by suction filtration to give 1.6 g of (1'R,2'S,5'R)-menthyl-5R-acetoxy-1,3-oxathiolane-2R-carboxylate: m.p. 105.2° C.; $[\alpha]_D$–60° (c, 0.51, CHCl$_3$); $^1$H NMR (CDCl$_3$) δ0.77 (d, 3H, J=7 Hz), 0.91 (d, 3H, J=7 Hz), 0.92 (d, 3H, J=7 Hz), 0.86–2.06 (m, 9H), 2.10 (s, 3H), 3.16 (d, 1H, J=12 Hz), 3.44 (dd, 1H, J=4, 12 Hz), 4.74 (dt, 1H, J=5, 12 Hz), 5.63 (s, 1H), 6.79 (d, 1H, J=4 Hz); $^{13}$C NMR (CDCl$_3$) δ16.16, 20.74, 21.11, 21.97, 23.29, 26.08, 31.38, 34.13, 37.24, 40.62, 47.07, 76.11, 79.97, 99.78, 168.60, 169.68.
Method B A mixture of the four diastereomers of formula (X) (300 mg) was dissolved in n-pentane containing a minimum amount of diethyl ether and was kept at –20° C. for 24 hours. The white needles formed were filtered quickly while cold to give 25 mg of material. The substance thus isolated was found to be identical in all respects with those obtained by Method A or C.
Method C A solution of dicyclohexylcarbodiimide (1.362 g, 6.6 mmol) in dichloromethane (5 mL) was added to a 50 mL round bottom flask containing a solution of trans-5-acetoxy-1,3-oxathiolane-2-carboxylic acid (1.16 g, 6.04 mmol), (1R,2S,5R)-(–)-menthol (1.038 g, 6.60 mmol), and 4-dimethylaminopyridine (75 mg, 0.62 mmol) in dichloromethane (10 mL) at 0° C. The resulting white slurry was stirred at room temperature for 3 hours at which time methanol (0.2 mL) and glacial acetic acid (0.2 mL) were added. After stirring for 10 minutes, the reaction mixture was diluted with hexanes (25 ml), filtered through Celite, and concentrated. The crude product thus obtained was dissolved in hexanes (25 mL), filtered through Celite and concentrated to provide 1.98 g (100%) of (1'R,2'S,5'R)-menthyl-5R-acetoxy-1,3 -oxathiolane-2R-carboxylate and (1'R,2'S,5'R)-menthyl-5S-acetoxy-1,3-oxathiolane-2S-carboxylate: $^1$H NMR (CDCl$_3$) δ0.75 (d, 3H, J=7 Hz), 0.78 (d, 3H, J=7 Hz), 0.85–0.92 (m, 12H), 0.95–2.19 (m, 18H), 2.10 (s, 6H), 3.15 (d, 2H, J=12 Hz), 3.42 (dd, 1H, J=4, 12 Hz), 3.44 (dd, 1H, J=4, 12 Hz),4.74 (dt, 2H, J=5, 12 Hz), 5.61 (s, 1H), 5.62 (s, 1H), 6.65 (s, 2H)

The above mixture of diastereoisomers was dissolved in petroleum ether (40°–60° C.) containing a minimum amount of diethyl ether and was cooled in a dry ice-acetone bath. The white solid precipitate was immediately collected (620 mg) by suction filtration. This material was recrystallized again under the same conditions to yield 450 mg of a white solid. This compound was found to be identical in all respects to those prepared using either method A or method B.

EXAMPLE 9

(1'S,2'R,5'S)-MENTHYL-5S-ACETOXY-1,3-OXATHIOLANE-2S-CARBOXYLATE

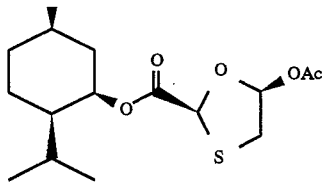

(X)

A solution of dicyclohexylcarbodiimide (491 mg, 2.38 mmol) in dichloromethane (7 mL) was added to a 50 mL round bottom flask containing a solution of trans-5-acetoxy-1,3-oxathiolane-2-carboxylic acid (IX) (416 mg, 2.2 mmol), (1S,2R,5S)-(+)-menthol (372 mg, 2.38 mmol), and 4-dimethylamino-pyridine (26 mg, 0.21 mmol) in dichloromethane (5 mL) at 0° C. The resulting thick slurry was stirred at room temperature for 3 hours at which time methanol (0.2 mL) and glacial acetic acid (0.2 mL) were added. After stirring for 10 minutes, the mixture was diluted with hexanes (25 mL), filtered through Celite, and concentrated. The crude product obtained was dissolved in hexanes (25 mL), filtered through Celite, and concentrated to produce 0.715 mg (100%) of two diastereomers, namely (1'S,2'R,5'S)-menthyl-5S-acetoxy-1,3-oxathiolane-2S-carboxylate and (1'S,2'R,5'S)-menthyl-5R-acetoxy-1,3-oxathiolane-2R-carboxylate: $^1$H NMR (CDCl$_3$) δ0.75 (d, 6H, J=7 Hz), 0.85–0.92 (m, 12H), 0.95–2.19 (m, 18H), 2.10 (s, 6H), 3.15 (d, 2H, J=12 Hz), 3.42 (dd, 1H, J=4, 12 Hz), 3.44 (dd, 1H, J=4, 12 Hz), 4.72 (dr, 2H, J=5, 12 Hz) 5.61 (S, 1H), 5.62 (S, 1H), 6.65 (S, 2H).

The above diastereomeric acetoxy menthyl esters mixture was dissolved in petroleum ether (40°–60° C.) containing a minimum amount of diethyl ether and was cooled in a dry ice-acetone bath. The white solid precipitate was immediately collected (200 mg) by suction filtration. This material was recrystallized again under the same conditions to yield 130 mg (34% based on one enantiomer) of (1'S,2'R,5'S)-menthyl-5S-acetoxy-1,3-oxathiolane-2S-carboxylate: m.p. 104.2° C.; $[\alpha]_D$+59.2° (c, 1.02, CHCl$_3$); $^1$H NMR (CDCl$_3$) δ0.77 (d, 3H, J=7 Hz), 0.91 (d, 3H, J=7 Hz), 0.92 (d, 3H, J=7 Hz), 0.86–2.06 (m, 9H), 2.10 (s, 3H), 3.16 (d, 1H, J=12 Hz), 3.44 (dd, 1H,J=4, 12 Hz), 4.74 (dt, 1H, J=5, 12 Hz), 5.63 (s, 1H), 6.79 (d, 1H., J=4 Hz); $^{13}$C NMR (CDCl$_3$) δ16.16, 20.74, 21.11, 21.97, 23.29, 26.08, 31.38, 34.13, 37.24, 40.62, 47.07, 76.11, 79.96, 99.78, 168.60, 169.68.

EXAMPLE 10

(1'R,2'S,5'R)-MENTHYL-5R-ACETOXY-1,3-OXATHIOLANE-2S-CARBOXYLATE

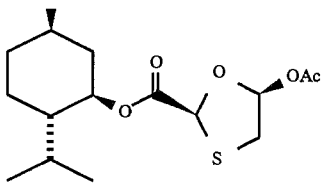

(X)

(1'R,2'S,5'R)-Methyl-5R-acetoxy-1,3-oxathiolane-2S-carboxylate was prepared by the following two methods.

Method A

A saturated solution of a mixture of the four diastereomers (12.28 g), obtained in Example 7, was prepared in petroleum ether containing a minimum amount of diethyl ether and was kept at −20° C. for 72 hours. The white crystalline solid produced was isolated by filtration to give 1.6 g of (1'R,2'S, 5'R)-menthyl-5R-acetoxy-1,3-oxathiolane-2S-carboxylate: m.p. 110.2° C.; [α]$_D$−177° (c, 0.7, CHCl$_3$); $^1$H NMR (CDCl$_3$) δ0.75 (d, 3H, J=7 Hz), 0.88 (d, 3H, J=7 Hz), 0.92 (d, 3H, J=7 Hz), 0.97–2.02 (m, 9H), 2.12 (s, 3H), 3.22 (d, 1H, J=11 Hz), 3.29 (dd, 1H J=4, 11 Hz), 4.74 (dt, 1H, J=4, 11 Hz), 5.63 (s, 1H), 6.65 (d, 1H, J=3 Hz); $^{13}$C NMR (CDCl$_3$) δ16.9, 20.69, 21.19, 21.95, 23.29, 26.10, 31.34, 34.0, 37.62, 40.32, 46.82, 75.69, 80.20, 99.36, 168.55, 170.23.

Method B

A solution of dicyclohexylcarbodiimide (118 mg, 0.572 mmol) in dichloromethane (5 mL) was added to a 25 mL round bottom flask containing a solution of cis-5-acetoxy-1,3-oxathiolane-2-carboxylic acid (100 mg, 0.52 mmol), (1R,2S,5R)-(−)-menthol (85 mg, 0.54 mmol), and 4-dimethyl-aminopyridine (DMAP) (8 mg, 0.053 mmol) in dichloromethane (10 ml) at 0° C. The resulting white slurry was stirred at room temperature for 3 hours at which time methanol (0.1 mL) and glacial acetic acid (0.1 mL) was added. After stirring for 10 minutes, the mixture was diluted with hexanes (15 mL), filtered through Celite, and concentrated. The crude product obtained was dissolved in hexanes (15 mL), filtered through Celite, and concentrated to yield 170 mg (100%) of (1'R,2'S,5'R)-menthyl-5R-acetoxy-1,3-oxathiolane-2S-carboxylate and (1'R,2'S,5'R)-menthyl-5S-acetoxy-1,3-oxathiolane-2R-carboxylate: $^1$H NMR (CDCl$_3$) δ0.75 (d, 3H, J=7 Hz), 0.78 (d, 3H, J=7 Hz), 0.88–0.94 (m, 12H), 0.97–2.03 (m, 18H), 2.10 (s, 3H), 2.13 (s, 3H), 3.23–3.30 (m, 4H), 4.65–4.75 (m, 2H), 5.63 (s, 1H), 5.64 (s, 1H), 6.64 (m, 2H).

The above mixture of diastereomers was recrystallized from petroleum ether (40°–60° C.) and a minimum amount of diethyl ether at room temperature. The white crystalline material formed was collected (95 mg) by filtration. This material was recrystallized again from diethyl ether-petroleum ether to yield 74 mg (78% based on one enantiomer) of (1'R,2'S,5'R) menthyl-5R-acetoxy-1,3-oxathiolane-2S-carboxylate.

EXAMPLE 11

(1'S,2'R,5'S)-MENTHYL-5S-ACETOXY-1,3-OXATHIOLANE-2R-CARBOXYLATE

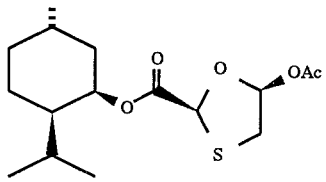

(X)

A solution of dicyclohexylcarbodiimide (1.588 g, 7.7 mmol) in dichloromethane (7 mL) was added to a 50 ml round bottom flask containing a solution cis-5-acetoxy-1,3-oxathiolane-2-carboxylic acid (1.36 g, 7 mmol), (1S,2R,5S)-(+)-menthol (1.216 g, 7.7 mmol), and 4-dimethylamino-pyridine (85 mg, 0.7 mmol) in dichloromethane (16 mL) at 0° C. The resulting thick slurry was stirred at room temperature for 3 hours. The reaction was quenched with methanol (0.4 mL) and glacial acetic acid (0.4 mL) and the mixture was stirred for 10 min. The resultant mixture was diluted with hexanes (25 mL), filtered through a pad of Celite, and concentrated. The crude material thus obtained was redissolved in hexanes (25 mL) and filtered through Celite. Removal of the solvent under reduced pressure yielded 2.3 g of a white solid (100%) which consisted of (1,S,2,R,5,S)-menthyl-5S-acetoxy-1,3-oxathiolane-2R-carboxylate and (1,S,2'R,5'S)-menthyl-5R-acetoxy-1,3-oxathiolane-2S-carboxylate:

$^1$H NMR (CDCl$_3$) δ0.75 (d, 3H, J=7 Hz), 0.78 (d, 3H, J=7 Hz), 0.88–0.94 (m, 12H), 0.97–2.03 (m, 18H), 2.10 (s, 3H), 2.13 (s, 3H), 3.23–3.30 (m, 4H), 4.65–4.74 (m, 2H), 5.63 (s, 1H), 5.64 (s, 1H), 6.64 (m, 2H).

The above mixture of diastereomers was recrystallized from petroleum ether (40°–60° C.) and a small amount of diethyl ether at room temperature to give 1.3 g of a white solid. This material was recrystallized again from diethyl ether-petroleum ether (40°–60° C.) to give 900 mg (78% based on one enantiomer) of (1'S,2'R,5'S)-menthyl-5S-acetoxy-1,3-oxathiolane-2R-carboxylate: m.p. 110.2° C.; [α]$_D$+177° (C, 1.0, CHCl$_3$); $^1$H NMR (CDCl$_3$) δ0.75 (d, 3H, J=7 Hz), 0.89 (d, 3H, J=7Hz), 0.92 (d, 3H, J=7 Hz), 0.98–2.02 (m, 9H), 2.12 (s, 3H), 3.22 (d, 1H, J=11 Hz), 3.29 (dd, 1H, J=4, 11 Hz), 4.74 (dt, 1H, J=11, 4 Hz), 5.63 (s, 1H), 6.65 (d, 1H, J=3 Hz); $^{13}$C NMR (CDCl$_3$) δ16.9, 20.69, 21.19, 21.95, 23.29, 26.10, 31.34, 34.09, 37.62, 40.32, 46.82, 75.79, 80.20, 99.36, 168.55, 170.23.

EXAMPLE 12

(1'R,2'S,5'R)-MENTHYL-5S-(CYTOSIN-1"-YL)-1,3-OXATHIOLANE-2R-CARBOXYLATE

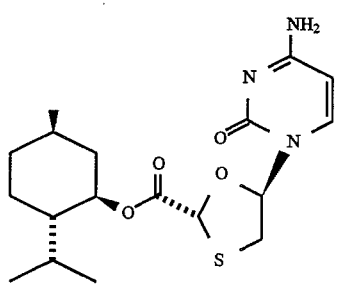

(XI)

t-Butyl-dimethylsilyl trifluoromethanesulfonate (1.1 mL, 4.79 mmol) was added to a suspension of cytosine (0.27 g, 2.5 mmol) in CH$_2$Cl$_2$ (2 mL) containing 2,4,6-collidine (0.65 ml, 4.92 mmol) at room temperature. The resultant mixture was stirred for 15 minutes and a clear solution was produced. A solution of (1'R,2'S,5'R)-menthyl-5S-acetoxy-1,3-oxathiolane-2R-carboxylate (0.66 g, 1.99 mmol) in methylene chloride (1.5 mL) was added to the mixture and stirring was continued for 5 minutes. Iodotrimethylsilane (0.31 mL, 2.18 mmol) was introduced dropwise and a white precipitate was produced when the addition was completed. The reaction mixture was allowed to stir for 18 hours. The reaction was quenched by addition of a saturated aqueous solution of Na$_2$S$_2$O$_3$ (10 mL) and CH$_2$Cl$_2$ (30 mL). The organic layer was separated and washed with brine (2×10 mL). The solvent was removed in vacuo to give a viscous oil which was suspended in diethyl ether (30 mL). To this suspension was added a saturated aqueous solution of NaHCO$_3$ (20 mL) with vigorous stirring. A white precipitate appeared and the resultant suspension was diluted with hexanes (10 mL). The precipitate was collected by filtration to give 0.57 g (75%) of a white solid. The $^1$H NMR spectrum of this material indicated that it was a mixture of the cis- and trans- diastereomers of the expected nucleoside in a 23:1 ratio.

This product was purified further by recrystallization from EtOAc-hexanes-MeOH: [α]$_D$–144° (c, 1.02, CHCl$_3$); m.p. 219° C. (decomposed); $^1$H NMR (CDCl$_3$) δ0.76 (d, 3H, J=7 Hz), 0.85–0.94 (m, 6H), 1.02–1.10 (m, 2H), 1.42–2.06 (m, 7H), 3.14 (dd, 1H, J=6.6, 12.1 Hz), 3.54 (dd, 1H, J=4.7, 12.1 Hz), 4.72–4.78 (m, 1H), 5.46 (s, 1H), 5.99 (d, 1H, J=7.5 Hz), 8.43 (d, 1H, J=7.6 Hz); $^{13}$C (CDCl$_3$) δ16.1, 20.7, 21.9, 23.2, 26.4, 31.4, 34.0, 36.3, 40.7, 47.1, 76.7, 78.4, 90.3, 94.6, 141.8, 155.4, 165.6, 169.8.

EXAMPLE 13

(1'S,2'R,5'S)-MENTHYL-5S-(CYTOSIN-1"-YL)-1,3-OXATHIOLANE-2R-CARBOXYLATE

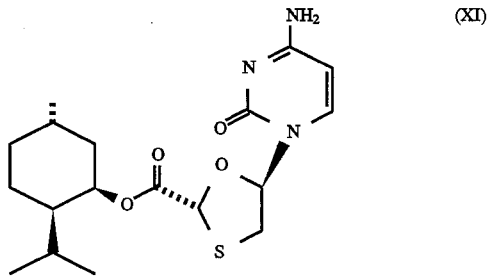

2,4,6-Collidine (0.317 mL, 2.4 mmol) and t-butyldimethylsilyl trifluoromethanesulfonate (0.551 mL, 2.4 mmol) were added successively to a suspension of cytosine (133.3 mg, 1.2 mmol) in CH$_2$Cl$_2$ (1 mL) at room temperature under an argon atmosphere. The resultant mixture was stirred for 15 minutes to produce a clear solution. A solution of (1'S,2'R,5'S)-menthyl-5S-acetoxy-1,3-oxathiolane-2R-carboxylate (330 mg, 1 mmol) in CH$_2$Cl$_2$ (0.5 mL) was introduced, followed by iodotrimethylsilane (0.156 ml, 1.1 mmol). The resultant mixture was stirred for 3 hours. The mixture was diluted with CH$_2$Cl$_2$ (20 mL) and washed successively with saturated aqueous NaHSO$_3$, water, and brine. The solvent was evaporated and the residue was taken up in ether-hexanes (1:1, 10 mL) and saturated aqueous NaHCO$_3$ (2 mL). Stirring was continued for 15 minutes. The aqueous layer was removed and the organic phase was centrifuged to give a white solid which was washed with hexanes (3×5 mL) and dried under vacuum. This substance, namely (1'S,2'R,5'S) -menthyl-5S-(cytosin-1"-yl)-1,3-oxathiolan-2R-carboxylate (380 mg, 100%) was contaminated with about 3% of (1'S,2'R,5'S) -menthyl-5R-(cytosin-1"-1,3-oxathiolan-2R-carboxylate (as indicated by its $^1$H NMR spectrum), was recrystallized from MeOH to give (1'S,2'R,5'S)-menthyl-5S-(cytosin-1"-yl)-1,3-oxathiolane-2R-carboxylate: [α]$_D$–58° (c, 0.506, CHCl$_3$); m.p.: 235° C. (decomposed)); $^1$H NMR (CDCl$_3$) δ0.80 (3H), 0.92 (6H), 1.06 (2H), 1.37–2.10 (7H), 3.11 (1H), 3.55 (1H), 4.77 (1H), 5.47 (1H), 5.79 (1H), 6.49 (1H), 8.37 (1H); $^{13}$C NMR (CDCl$_3$) δ6.8, 21.3. 22.5, 23.9, 26.8, 32.0, 34.6, 37.0, 40.7, 47.4, 77.3, 79.3, 90.9, 95.3, 142.9, 155.1, 164.9, 170.1.

EXAMPLE 14

(1'R,2'S,5'R)-MENTHYL-5R-(CYTOSIN-1"-YL)-1,3-OXATHIOLANE-2S-CARBOXYLATE

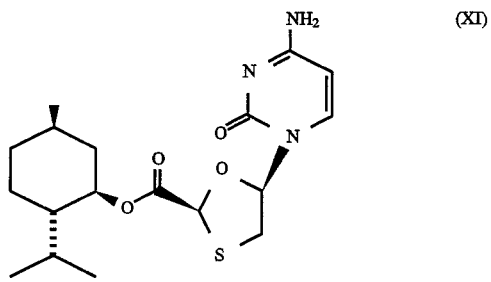

2,4,6-collidine (0.317 mL, 2.4 mmol) and t-butyldimethylsilyl trifluoromethanesulfonate (0.551 mL, 2.4 mmol) were added successively to a suspension of cytosine (133.3 mg, 1.2 mmol) in CH$_2$Cl$_2$ (1 mL) at room temperature under an argon atmosphere. The resultant mixture was stirred for 15 minutes and a clear solution was obtained. A solution of (1'R,2'S,5'R)-menthyl-5R-acetoxy-1,3-oxathiolan-2S-carboxylate (330 mg, 1 mmol) in CH$_2$Cl$_2$ (0.5 mL) was introduced, followed by iodotrimethylsilane (0.156 mL, 1.1 mmol). Stirring was continued for 3 hours. The mixture was diluted with CH$_2$Cl$_2$ (20 mL) and washed successively with saturated aqueous NaHSO$_3$, water, brine and then was concentrated. The residue was taken up in ether-hexanes (1:1, 10 mL) and saturated aqueous NaHCO$_3$ (2 mL) and was stirred at room temperature for 15 minutes. The aqueous layer was removed and the organic phase was centrifuged to yield a white solid which was washed with hexanes (3×5 mL) and then dried under vacuum. The product (1',R,2'S,5'R)-menthyl-5R-(cytosin-1"-yl)-1,3-oxathiolan-2S-carboxylate (336.3 mg, 88%) contained about 6% of (1'R,2'S,5'R)-menthyl-5S-(cytosin-1"-yl)-1,3-oxathiolan-2S-carboxylate (NMR). This material was recrystallized from MeOH to give the desired product: [α]$_D$+56° (c, 1.08, CHCl$_3$); m.p.: 235° C. (decomposed); $^1$H NMR (CDCl$_3$) δ0.80 (3H) 0.91 (6H), 1.00 (2H), 1.37–2.10 (7H), 3.11 (1H), 3.55 (1H), 4.77 (1H), 5.47 (1H), 5.79 (1H), 6.49 (1H), 8.37 (1H); $^{13}$C NMR (CDCl$_3$) δ16.8, 21.3. 22.5, 23.9, 26.8, 32.0, 34.6, 36.8, 40.7, 47.4, 77.1, 78.8, 90.9, 95.6, 141.9, 156.3, 166.6, 170.2.

EXAMPLE 15

(1,S,2,R,5'S)-MENTHYL-5R-(CYTOSIN-1"-YL)-1,3-OXATHIOLANE-2S-CARBOXYLATE

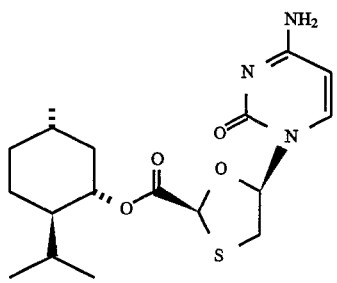

(XI)

2,4,6-collidine (0.106 mL, 0.8 mmol) and t-butyldimethylsilyl trifluoromethanesulfonate were added successively to a suspension of cytosine (44 mg, 0.4 mmol) in $CH_2Cl_2$ (0.5 mL) at room temperature under an argon atmosphere. Stirring was continued at room temperature for 15 minutes and a clear solution was produced. A solution of (1'S,2'R,5'S)-menthyl-5S-acetoxy-1,3-oxathiolan-2S-carboxylate (110 mg, 0.33 mmol) in $CH_2Cl_2$ (0.3 mL) was added, followed by iodotrimethylsilane (0.052 mL, 0.36 mmol). The resultant mixture was stirred at room temperature overnight and then was diluted with $CH_2Cl_2$ (10 mL). The mixture was washed successively with saturated aqueous $NaHSO_3$, water, brine and concentrated under reduced pressure. The residue was taken up in ether-hexanes (1:1, 5 mL) and saturated aqueous $NaHCO_3$ (1 mL) and stirring was continued at room temperature for 20 minutes. The aqueous layer was removed and the white solid suspended in the organic phase was collected by centrifugation. This solid was washed with hexanes (3×5 mL) and dried under vacuum to provide 65 mg (51.2%) of (1,S,2,R,5'S)-menthyl-5R-(cytosin-1"-yl)-1,3-oxathiolan-2S-carboxylate contaminated with approximately 5% of (1'S,2'R,5'S)-menthyl-5S-(cytosin-1"-yl)-1,3-oxathiolan-2S-carboxylate as indicated by $^1H$ NMR spectroscopy. Recrystallization of the crude material from $MeOH-Et_2O$ gave the desired product: m.p. 210°–211° C.; $[\alpha]_D+179°$ (c, 0.66, $CHCl_3$); $^1H$ NMR ($CDCl_3$) δ0.77 (3H) 0.92 (6H), 1.00 (2H), 1.37–2.10 (6H), 3.14 (1H), 3.55 (1H), 4.76 (1H), 5.46 (1H), 5.88 (1H), 6.46 (1H), 8.38 (1H); $^{13}C$ NMR ($CDCl_3$) δ16.8, 21.3. 21.8, 22.5, 23.9, 26.7, 31.9, 34.7, 38.7, 40.9, 47.4, 76.4, 80.8, 100.0, 169.1, 170.8

The washings and the supernatant were combined and washed with 1N HCl, water, brine, and then was dried over $Na_2SO_4$. Evaporation of the solvent yielded 53 mg (48%) of unreacted (1'S,2'R,5'S)-menthyl-5S-acetoxy-1,3-oxathiolan-2S-carboxylate.

EXAMPLE 16

2R-HYDROXYMETHYL-5S-(CYTOSIN-1'-YL)-1,3-OXATHIOLANE

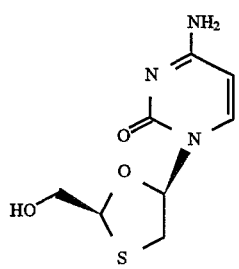

(XII)

A solution of (1'R,2'S,5'R)-menthyl-5S-(cytosin-1"-yl)-1,3-oxathiolane-2R-carboxylate (67 mg, 0.18 mmol) in THF (1 mL) was slowly added to a stirred suspension of lithium aluminum hydride (19 mg, 0.5 mmol) in THF (2 mL) at ambient temperature under an argon atmosphere. Stirring was continued for 30 minutes. The reaction was then quenched with methanol (3 mL), followed by the addition of silica gel (5 g). The resultant slurry was stirred for 30 minutes and then was transferred to a short column packed with Celite and silica gel and was eluted with a 1:1:1 mixture of EtOAc-hexane-methanol (50 mL). The eluate was concentrated and subjected to silica gel column chromatography (EtOAc-hexane-methanol, 1:1:1) to give a gummy solid. This solid was dried azeotropically with toluene to give 38 mg (94%) of the desired product: $[\alpha]_D-122°$ (C, 1.01, MeOH); m.p. 128°–130° C.; $^1H$ NMR ($CD_3OD$) δ3.05 (dd, 1H, J=4.3, 11.9 Hz) 3.42 (dd, 1H, J=5.3, 11.9 Hz), 3.76–3.89 (m, 2H), 5.19–5.21 (m, 1H), 5.81 (d, 1H, J=7.6 Hz), 6.20–6.23 (m, 1H), 7.01–7.16 (brm, 2H, exchangeable), 7.98 (d, 1H, J=7.5 Hz); $^{13}C$ ($CD_3OD$) δ38.5, 64.1, 88.0, 88.9, 95.7, 142.8, 157.9, 167.7.

EXAMPLE 17

2S-HYDROXYMETHYL-5R-(CYTOSIN-1'-YL)-1,3-OXATHIOLANE

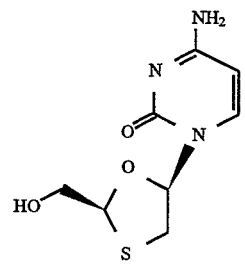

(XII)

A solution of (1'R,2'S,5'R)-menthyl-5R-(cytosin-1"-yl)-1,3-oxathiolane-2S-carboxylate (102 mg, 0.27 mmol) in THF (3 mL) was slowly added to a stirred suspension of lithium aluminum hydride (20 mg, 0.54 mmol) in THF (2 mL) at ambient temperature under an argon atmosphere. Stirring was continued for 30 minutes and the reaction was quenched with methanol (5 mL), followed by the addition of silica gel (7 g). The resultant slurry was stirred for 30 minutes, transferred to a short column packed with Celite and silica gel and was eluted with a 1:1:1 mixture of EtOAc-hexane-MeOH (50 mL). The eluate was concentrated and subjected to silica gel column chromatography (EtOAc-hexane-MeOH, 1:1:1) to provided a gummy solid which was dried azeotropically with toluene to give 50 mg (82%) of a white solid as the product: $[\alpha]_D+125°$ (c, 1.01, MeOH); m.p. 130°–132° C.; $^1H$ NMR ($CD_3OD$) δ3.05 (dd, 1H, J=4.3, 11.9 Hz), 3.42 (dd, 1H, J=5.3, 11.9 Hz), 3.76–3.89 (m, 2H), 5.19–5.21 (m, 1H), 5.81 (d, 1H, J=7.6 Hz), 6.20–6.23 (m, 1H), 7.01–7.16 (brm, 2H, exchangeable), 7.98 (d, 1H, J=7.5 Hz); $^{13}C$ ($CD_3OD$) δ38.5, 64.1, 88.0, 88.9, 95.7, 142.8, 157.9, 167.7.

EXAMPLE 18

(1'R,2'S,5'R)-MENTHYL-5R-(5'-FLUOROCYTOSIN-1"-YL)-1,3-OXATHIOLANE-2S-CARBOXYLATE

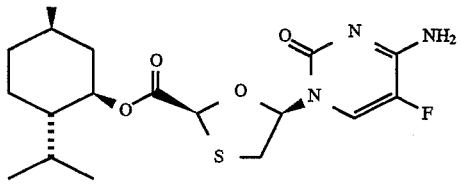

To a suspension of 5-fluorocytosine (155 mg, 1.2 mmol) in CH$_2$Cl$_2$ (1 mL) at room temperature under an argon atmosphere was added, successively, 2,4,6-collidine (0.317 mL, 2.4 mmol) and t-butyldimethylsilyl trifluoromethanesulfonate (0.551 mL, 2.4 mmol). The resultant mixture was stirred for 15 minutes and a clear solution was obtained. A solution of (1'R,2'S,5'R)-menthyl-5R-acetoxy-1,3-oxathiolane-2S-carboxylate (330 mg, 1 mmol) in CH$_2$Cl$_2$ (0.5 mL) was introduced, followed by iodotrimethylsilane (0.156 mL, 1.1 mmol). Stirring was continued for 3 hours. The mixture was diluted with CH$_2$Cl$_2$ (20 mL) and washed successively with saturated aqueous NaHSO$_3$, water, brine and then was concentrated. The residue was taken up in ether-hexanes (1:1, 10mL) and saturated aqueous NaHCO$_3$ (2 mL) and stirred at room temperature for 15 minutes. The aqueous layer was removed and the organic phase was centrifuged to afford a white solid which was washed with hexanes (3×5 mL) and then dried under vacuum. The product (1'R,2'S,5'R)-menthyl-5R-(5"-fluorocytosin-1"-yl)-1,3-oxathiolane-2S-carboxylate (350 mg, 88%) thus obtained contained about 6% of (1'R,2'S,5'R)-menthyl-5S-(5"-fluorocytosin-1"-yl)-1,3 -oxathiolane-2S-carboxylate (NMR). This material was recrystallized from MeOH/CH$_2$Cl$_2$/benzene to give a crystalline product: [α]$_D^{26}$+22° (C, 0.19, MeOH); m.p. 216°–218° C., $^1$H NMR (CDCl$_3$) δ0.78 (d, 3H, J=7Hz), 0.91 (t, 6H, J=7.3 Hz), 1.00 (m, 2H), 1.39–2.04 (m, 7H), 3.12 (dd, 1H, J=6.6 Hz, 6.1 Hz), 3.52 (dd, 1H, J=4.7 Hz, 6.1 Hz), 4.79 (dt, 1H, J=4.4 Hz, 4.3 Hz), 5.46 (S, 1H), 5.75 (bs, 1H, exchangeable), 6.42 (5t, 1H, J=5.0 Hz), 8.10 (bs, 1H, exchangeable), 8.48 (d: 1H, J=6.6 Hz); $^{13}$C NMR (CDCl$_3$-DMSO-d$_6$): δ16.7, 21.2, 22.4, 23.7, 26.6, 31.8, 34.4, 36.6, 40.5, 47.2, 77.1, 79.1, 90.8, 126.3 (d, J=33 Hz), 137.1 (d, J=244 Hz), 154.2, 158.3 (d, J=15 Hz), 170.1.

EXAMPLE 19

(1'S,2'R,5'S)-MENTHYL-5S-(5"-FLUOROCYTOSIN-1"-YL)-1,3-OXATHIOLANE-2R-CARBOXYLATE

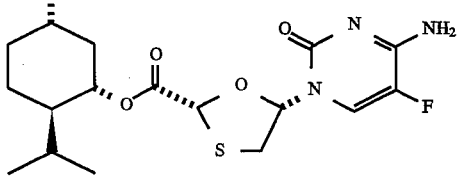

To a suspension of 5-fluorocytosine (180.0 mg, 1.4 mmol) in CH$_2$Cl$_2$ (1 mL) at room temperature under an argon atmosphere was added, successively, 2,4,6-collidine (0.46 mL, 3.5 mmol) and t-butyldimethylsilyl trifluoromethanesulfonate (0.67 mL, 2.9 mmol). The resultant mixture was stirred for 15 minutes and a clear solution was obtained. A solution of (1,S,2'R,5'S)-menthyl-5S-acetoxy-1,3-oxathiolane-2R-carboxylate (414 mg, 1.25 mmol) in CH$_2$Cl$_2$ (0.6 mL) was introduced, followed by iodotrimethylsilane (0.18 mL, 1.27 mmol). The resultant mixture was stirred for 1 hour. The mixture was diluted with CH$_2$Cl$_2$ (20 mL) and washed successively with saturated aqueous NaHSO$_3$, water, and brine. The solvent was evaporated and the residue was taken up in ether-hexanes (1:1, 10 mL) and saturated aqueous NaHCO$_3$ (2 mL). Stirring was continued for 15 minutes. The aqueous layer was removed and the organic phase was centrifuged to give a white solid which was washed with hexanes (3×5 mL) and dried under vacuum. This substance, namely (1,S,2,R,5,S)-menthyl-5S-(5"-fluorocytosin-1"-yl)-1,3-oxathiolane-2R-carboxylate (454 mg, 91%) contained about 7% of (1,S,2,R,5'S)-menthyl-5R-(5"-fluorocytosin-1"-yl)-1,3-oxathiolane-2R-carboxylate (as indicated by its $^1$H NMR sepctrum), was recrystallized from benzene CH$_2$Cl$_2$—MeOH to give the title compound: [α]$_D^{26}$–20° (c, 0.072,MeOH); m.p. 220°–222° C. (decomposed), $^1$H NMR (CDCl$_3$) δ0.80 (d, 3H, J=7 Hz), 0.90 (t, 6H, J=7 Hz), 1.0 (m, 2H), 1.39–2.04 (m, 7H), 3.12 (dd, 1H, J=6.6 and 6 Hz), 3.52 (dd, 1H, J=5 and 6 Hz), 4.8 (dt, 1H, J=4.4 and 4.3 Hz), 5.46 (s, 1H), 5.78 (bs, 1H, exchangeable), 6.42 (t, 1H, J=5 Hz), 8.1 (bs, 1H exchangeable), 8.5 d, 1H, J=6.6 Hz); $^{13}$C (CDCl$_3$) δ16.2, 20.7, 21.9, 23.3, 26.2, 31.4, 34.0, 36.3, 40.1, 46.8, 76.7, 78.7, 90.5, 125.9 (d. J=33 Hz), 136.5 (d, J=242 Hz), 153.7, 158.2 (d, J=14 Hz), 169.6.

EXAMPLE 20

2S-HYDROXYMETHYL-5R-(5'-FLUOROCYTOSIN-1'-YL)-1,3-OXATHIOLANE

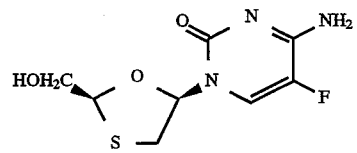

To a suspension of lithium aluminum hydride (10 mg, 0.54 mmol) in THF (1 mL) at ambient temperature under an argon atmosphere was slowly added a solution of (1'R,2'S, 5'R)-menthyl-5R-(5"-fluorocytosin-1"-yl)-1,3-oxathiolane-2S-carboxylate (54 mg, 0.135 mmol) in THF (2 mL). The reaction mixture was allowed to stir for 30 minutes, then quenched with excess methanol (2 mL), followed by the addition of silica gel (3 g). The resultant slurry was subjected to silica gel column chromatography (EtOAc-Hexane-MeOH, 1:1:1) to provide a gummy solid which was dried azeotropically with toluene to give 20.7 mg (63%) of a white solid as the product: [α]$_D^{26}$+114° (C, 0.12, MeOH); $^1$H NMR (DMSO-d6) δ3.14 (dd, 1H, J=4.3, 11.9 Hz), 3.42 (dd, 1H J=5.3, 11.9 Hz), 3.76 (m,2H), 5.18 (m, 1H), 5.42 (t, 1H, J=4.8 Hz), 6.14 (m, 1H), 7.59 (br m, 1H, exchangeable), 7.83 (br m, 1H exchangeable), 8.20 (d, 1H, J=7.66 Hz).

EXAMPLE 21

2R-HYDROXYMETHYL-5S-(5'-FLUOROCYTOSIN-1'-YL)-1,3-OXATHIOLANE

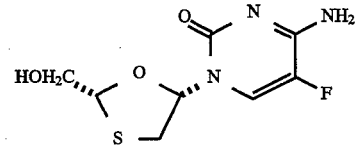

To a stirred THF (2 mL) suspension of lithium aluminum hydride (22 mg, 1.13 mmol) at ambient temperature under an argon atmosphere was slowly added a solution of (1'R, 2'S, 5'R)-menthyl-5S-(5"-fluorocytosin-1"-yl)-1,3-oxathiolane-2R-carboxylate (91 mg, 0.23 mmol) in THF (8 mL). The reaction mixture was allowed to stir for 2 hours, and was quenched by addition of methanol (3 mL), followed by silica gel (5 g). The resultant slurry was stirred for 30 minutes. The mixture was then passed through a short pad of Celite and silica gel eluted with a 1:1:1 mixture of EtOAc-hexane-Methanol (10×5 mL). The eluate was concentrated and subjected to silica gel column chromatography (EtOAc-hexane-methanol, 1:1:1) to give a gummy solid. This solid was dried azeotropically with toluene to give 45 mg (80%) of the desired product: $[\alpha]_D^{26}$ –119° (C, 1.01, MeOH); $^1$H NMR (DMSO-d$_6$) δ3.14 (dd, 1H, J=4.3, 11.9 Hz), 3.42 (dd, 1H, J=5.3, 11.9 Hz), 3.76 (m, 2H), 5.18 (m, 1H), 5.42 (t, 1H, J=4.8 Hz), 6.14 (m, 1H), 7.59 (br m, 1H, exchangeable), 7.83 (br m, 1H exchangeable), 8.20 (d, 1H J=7.66 Hz).

EXAMPLE 22

CIS-2(N-METHYL-N-METHOXYAMINOCARBONYL)-5-(URACIL-1'-YL)-1,3-OXATHIOLANE

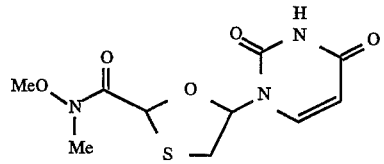

Trimethylsilyl trifluoromethanesulphonate (TMSOTf) (107 μL, 0.552 mmol) was introduced to a stirred suspension of uracil (31 mg, 0.276 mmol) in dichloromethane (1.5 mL) containing collidine (73 μL, 0.552 mmol) under argon atmosphere. The resultant mixture was stirred for 15 minutes to provide a homogeneous solution. A solution of trans-2-(N-methyl-N-methoxyaminocarbonyl)-5-acetoxy-1,3-oxathiolane (50 mg, 0.23 mmol) in dichloromethane (1 mL) was introduced, followed by iodotrimethylsilane (TMSI) (33 μL, 0.23 mmol). The reaction was allowed to proceed for 2.5 hours and then was quenched with a solution of saturated NaHCO$_3$ and Na$_2$S$_2$O$_3$ (1:1). The resulting mixture was stirred for 5 minutes and then was transferred to a separatory funnel with the aid of more dichloromethane. The aqueous phase was removed and the organic layer was washed with saturated Na$_2$S$_2$O$_3$, water, brine and then was dried (Na$_2$SO$_4$). Evaporation of the solvent under reduced pressure afforded the crude product which was triturated with EtOAc-Hexane (1:1) to give 54 mg (87%) of the title compound as a white solid; $^1$H NMR (CDCl$_3$): δ3.14 (d of d, 1H, J=8.0, 11.8 Hz), 3.23 (s, 3H), 3.38 (d of d, 1H, J=4.7, 11.8 Hz), 3.74 (s, 3H), 5.80 (d, 1H, J=8.2 Hz), 5.82 (s, 1H), 6.44 (d of d, 1H, J=4.7, 8.0 Hz), 8.64 (d, 1H, J=8.2 Hz), 9.64 (br s, 1H).

EXAMPLE 23

CIS- AND TRANS-2-BENZOYL-5-ACETOXY-1,3-OXATHIOLANE

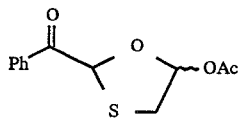

Phenyl glyoxal monohydrate (608 mg, 4.0 mmol) and 2,5-dihydroxy-1,4-dithiane (304 mg, 2.0 mmol) were heated for ca. 5 minutes at 65° C. until the reagents melted. The reaction mixture was diluted with dichloromethane (40 mL). Pyridine (1.32 μL, 16.0 mmol), 4-dimethylamino-pyridine (DMAP) (48 mg), and acetyl chloride (0.85 mL, 12.0 mmol) were added to the stirred solution at 0° C. The reaction mixture was stirred at room temperature for 4.5 hours and diluted with brine solution (15 mL). The organic layer was separated, washed with sodium bicarbonate and brine solutions, dried (sodium sulfate), and evaporated to a brown liquid (1.80 g). The residue was purified by silica gel chromatography eluting with hexanes:EtOAc (3:1) to yield the trans and cis isomers (2.4:1 ratio) (714 mg, 71%); $^1$H NMR (CDCl$_3$) δ2.0 (s, 3H), 2.14 (s, 3H), 3.15–3.25 (m, 1H), 3.35–3.45 (m, 1H), 6.42 (s, 1H), 6.51 (s, 1H), 6.7 (m, 1H), 6.9 (m, 1H), 7.4–7.5 (m, 2H), 7.55–7.65 (m, 1H), 7.9–8.0 (m, 2H).

EXAMPLE 24

CIS-2-(1'-PYRROLIDINOCARBONYL)-5-ACETOXY-1,3-OXATHIOLANE

To a solution of 5-acetoxy-oxathiolane-2-carboxylic acid (576 mg, 3.0 mmol), pyridine (0.533 mL, 6.60 mmol), and dichloromethane (20 mL) at 0° C., was added oxalyl chloride (0.314 mL, 3.6 mmol). The reaction was stirred at 0° C. for 30 minutes and then cooled to –70° C. at which time pyrrolidine (0.5 mL, 6.0 mmol) was added in one portion. The reaction was stirred at room temperature for 2 hours followed by addition of 1N HCl (5 mL). The organic layer was separated, washed with sodium bicarbonate and brine solutions, dried (sodium sulfate), and concentrated to yield 0.851 g of crude product. This residue was purified by silica gel chromatography eluting with EtOAc:hexanes (9:1) to give 616 mg (84%) of the desired product; $^1$NMR (CDCl$_3$) δ1.80–2.00 (m, 4H), 2.11 (s, 3H), 3.20–3.35 (m, 2H), 3.40–3.55 (m, 4H), 5.76 (s, 1H), 6.60 (m, 1H).

EXAMPLE 25

CIS-2-CARBOMETHOXY-5-(5'-BROMOURACIL-1'-YL)-1,3-OXATHIOLANE

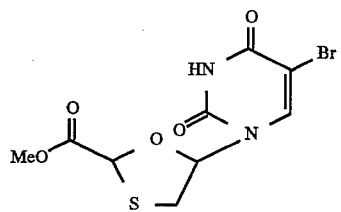

Bis-trimethylsilyl-acetamide (4 mL, 16.2 mmol) was added to a suspension of 5-bromouracil (1.5 g, 7.9 mmol) in dichloromethane (10 mL). The reaction was stirred for 30 minutes, yielding a clear solution. Then a dichloromethane solution (5 mL) of 2-carbomethoxy-5-acetoxy-1,3-oxathiolane (1.6 g, 7.8 mmol cis:trans 1:2) was added, followed by TMSI (1.1 mL, 7.7 mmol).

The reaction was stirred at ambient temperature for 18 hours and then sequentially treated with saturated aqueous solutions of Na$_2$S$_2$O$_3$ and NaHCO$_3$ to give a white suspension. The suspension was filtered to remove the solid (unreacted base). The filtrate was concentrated and triturated with EtOAc-Hex (1:1) to give white solid which was filtered, washed and dried to give 0.98 g (38%) of the product. $^1$H NMR (CDCl$_3$) δ3.2 (dd, 1H, J=7 and 12 Hz), 3.47 (dd, 1H, J=5 and 12 Hz), 3.87 (s, 1H), 5.50 (s, 1H), 6.42 (dd, 1H, J=5 and 7 Hz), 8.72 (s, 1H), 9.19 (br s, 1H).

EXAMPLE 26

CIS-2-HYDROXYMETHYL-5-(6'-CHLOROURACIL-1'-YL)-1,3-OXATHIOLANE

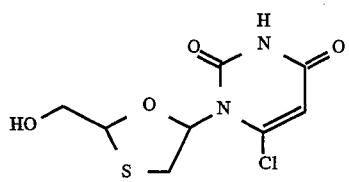

TMSOTf (4.5 mL, 27.3 mmol) was added to a suspension of bis-O-silyl-6-chlorouracil (9.5 g, 32.6 mmol) and 2-carbethoxy-5-acetoxyoxathiolane (6.3 g, 27.4 mmol) in 1,2-dichloroethane (40 mL). The resulting clear solution was heated slowly up to 60° C. and kept at this temperature for 1 hour, during which time a thick precipitate appeared. The reaction was cooled down to ambient temperature and the white precipitate was collected after filtration, washed and dried to give 3.5 g (42%) of the only cis nucleoside ester product ($^1$HNMR). To a tetrahydrofuran (THF) (50 mL) suspension of nucleoside ester product (2.6 g, 8.5 mmol), under argon atmosphere, was slowly added LiBH$_4$ (0.4 g, 18.6 mmol). The reaction was stirred for 5 hours, then quenched with methanol. The solvent was removed, followed by subjecting the resulting gummy material to column chromatography (2:2:1, EtOAc-Hex-MeOH, v/v) to yield 1.9 g (85%) of the title nucleoside. The overall yield of these two transformations was 64%; HPLC purity (96%); mp 202°–204° C.; $^1$H NMR (DMSO-d$_6$) δ3.09–3.30 (1H), 3.38–3.47 (1H), 3.60–3.72 (2H), 4.45 (1H), 5.05–5.09 (1H), 5.27 (1H), 5.59–5.62 (1H), 6.71–6.76 (1H); $^{13}$C NMR (DMSO-d$_6$) δ32.6, 63.2, 64.2, 84.7, 87.9, 94.4, 106.6, 128.6, 164.4.

EXAMPLE 27

(1'S,2'R,5'S)-MENTHYL-5S-(N-4"-ACETYLCYTOSIN-1"-YL)-1,3-OXATHIOLANE-2R-CARBOXYLATE

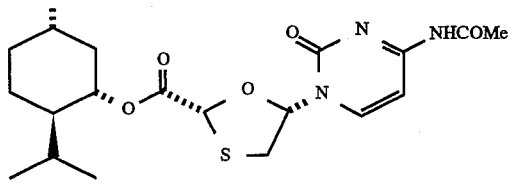

To a stirred suspension of N-4-acetylcytosine (68 mg, 0.4 mmol) in dichloromethane (0.5 mL) containing 2,4,6-collidine (105 μL, 0.8 mmol) under an argon atmosphere was added trimethylsilyl trifluoromethane-sulphonate (155 μL, 0.8 mmol). The resulting mixture was stirred for 15 minutes to give a homogeneous solution. The substrate, (1'S,2'R,5'S)-menthyl-5S-acetoxy-1,3-oxathiolane-2R-carboxylate (110 mg, 0.333 mmol) was introduced into the above solution in one batch. In a separate flask equiped with a condensor, a solution of hexamethyldisilazane (34 μL, 0.167 mmol) and iodine (42 mg, 0.167 mmol) in dichloromethane (0.5 mL) was refluxed under argon atmosphere for 30 minutes. After it had cooled to room temperature, the purple solution formed was transferred, via a syringe, into the mixture containing the substrate and silylated base.

The reaction mixture was kept at room temperature for 7 hours and then was quenched with a solution of a 1:1 mixture of saturated NaHCO$_3$ and Na$_2$S$_2$O$_3$. The resulting mixture was stirred for 5 minutes and then was transferred to a separatory funnel with the aid of more dichloromethane. The aqueous phase was removed and the organic layer was washed with saturated. Na$_2$S$_2$O$_3$, water, brine and then was dried (Na$_2$SO$_4$). The solvent was removed under reduced pressure to provide 153 mg of crude product. To determine the ratio of the cis-[(1'S,2'R,5'S)-menthyl-5S-(N-4"-acetylcytosin-1"-yl)-1,3-oxathiolane-2R-carboxylate] and trans-[(1'S,2'R,5'S)-menthyl-5R-(N-4"-acetylcytosin-1"-yl)-1,3-oxathiolane-2R-carboxylate] product isomers, the crude product was subjected to $^1$H NMR analysis in CDCl$_3$. Judging from the signals of the C6 protons of the cytosine moiety, the ratio of cis [δ8.70 (d, J=7.6 Hz)] to trans [δ7.79 (d, J=7.6 Hz)] was determined to be 7:1.

EXAMPLE 28

CIS-2-CARBOXYL-5-(URACIL-1'-YL)-1,3-OXATHIOLANE

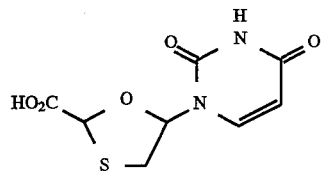

Iodotrimethylsilane (118 μL, 0.832 mmol) was added to a stirred suspension of bis-trimethylsilyluracil (122 mg, 0.475 mmol) and trans-2-carboxyl-5-acetoxy-1,3-oxathiolane (76 mg, 0.396 mmol) in dichloromethane (2.5 mL) containing collidine (53 μL, 0.396 mmol). The resultant mixture was stirred for 18 hours at room temperature under argon atmosphere and then was quenched by the addition of 5 mL of a 0.5M solution of sodium carbonate. The aqueous phase was acidified with 1M HCl solution to pH 4, followed by extraction with tetrahydrofuran (3×6 mL). The combined extract was dried over MgSO$_4$ and the solvent was removed under reduced pressure. The crude product obtained was triturated with dichloromethane to provide a white suspension. The white solid was isolated by centrifugation and was dried under vacuum to afford 27 mg of the desired product whose $^1$H NMR spectrum indicated the presence of a small amount of uracil (ca. 10%) and an isomeric purity of ≧95%. The title compound displayed the following spectral characteristics: $^1$H NMR (DMSO d$_6$) δ: 2.26 (d of d, 1H, J=4.9, 12.3 Hz), 3.49 (d of d, 1H, J=5.2, 12.4 Hz), 5.57 (s, 1H), 5.71 (d of d, 1H, J=2.2, 8.0 Hz; this signal collapsed to a doublet on treatment with D$_2$O (J=8.2 Hz)), 6.29 (t, 1H, J=5.2 Hz), 8.07 (d, 1H, J=8.2 Hz), 11.41 (br s, 1H, exchanged with D$_2$O).

EXAMPLE 29

CIS 2-(1'-PYRROLIDINOCARBONYL)-5-(URACIL-1'-YL)-1,3-OXATHIOLANE

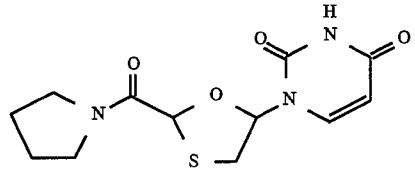

Iodotrimethylsilane (37 µL, 1 equivalent) was added to a stirred solution of cis 2-(1'-pyrrolidinocarbonyl)-5-acetoxy-1,3-oxathiolane (64 mg, 0.26 mmol) and bis-trimethylsilyluracil (80 mg, 1.2 equivalents) in dichloromethane (1.5 mL) under argon atmosphere. The reaction mixture was kept for 1 hour and 20 minutes at room temperature. The reaction was quenched with a solution of a 1:1 mixture of saturated $Na_2S_2O_3$ and $NaHCO_3$ (2 mL), followed by dilution with dichloromethane (4 mL). The resultant mixture was stirred for 5 minutes and then was transferred to a separatory funnel with the aid of more dichloromethane. The aqueous phase was removed and the organic phase was washed with water, brine, and dried over anhydrous $Na_2SO_4$. Removal of the solvent under reduced pressure and subjection of the crude product thus obtained to column chromatography (7% MeOH-EtOAc) afforded the 74 mg (95%) of the title compound; $^1$HNMR ($CDCl_3$): δ1.85–2.00 (m, 2H), 2.00–2.15 (m,2H), 3.25–3.70 (m, 6H), 5.61 (s, 1H), 5.80 (d of d, 1H, J=2.3, 8.2 Hz), 6.44 (d of d, 1H, J=4.8, 7.0 Hz), 8.29 (br s, 1H), 8.88 (d, 1H, J=8.1 Hz).

EXAMPLE 30

CIS 2-BENZOYL-5-(URACIL-1'-YL)-1,3-OXATHIOLANE

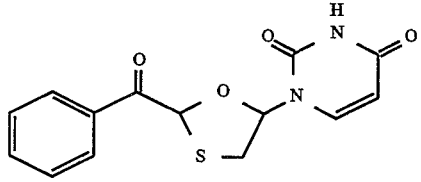

Trimethylsilyl trifluoromethanesulphonate (92 µL, 0.475 mmol) was introduced to a stirred suspension of uracil (50 mg, 0.238 mmol) in dichloromethane (1.5 mL) containing collidine (63 µL, 0.475 mmol) under argon atmosphere. The resultant mixture was stirred for 15 minutes to provide a homogeneous solution. A mixture (2.4:1, trans:cis) of 2-benzoyl-5-acetoxy-1,3-oxathiolane (50 mg, 0.198 mmol) was added as a solution in dichloromethane (1.5 mL), followed by iodotrimethylsilane (28 µL, 0.198 mmol). The reaction was allowed to proceed for 22 hours and then was quenched with a solution of a 1:1 mixture of saturated $NaHCO_3$ and $Na_2S_2O_3$. The resulting mixture was stirred for 5 minutes and then was transferred to a separatory funnel with the aid of more dichloromethane. The aqueous phase was removed and the organic layer was washed with saturated $Na_2S_2O_3$, water, brine and then was dried ($Na_2SO_4$). Thin layer chromatography analysis of the crude product indicated that small amount of the starting material remain unreacted. The crude product was triturated with EtOAc to provide 26 mg (43%) of the title compound as a white solid; $^1$H NMR (DMSO): δ3.19 (d of d, 1H, d of d, J=6.8, 12.1 Hz), 3.60 (d of d, 1H, J=5.1, 12.2 Hz), 5.77 (d, 1H, J=8.2 Hz), 6.38 (d of d, 1H, J=5.2, 6.9 Hz), 6.81 (s, 1H), 7.52–7.64 (m, 2H), 7.66–7.76 (m, 1H), 7.94–8.04 (m, 2H), 8.22 (d, 1H, J=8.1 Hz), 11.44 (br s, 1H).

EXAMPLE 31

(1'R,2'S,5'R)-MENTHYL-5S-(CYTOSIN-1"-YL)-1,3-OXATHIOLANE-2R-CARBOXYLATE

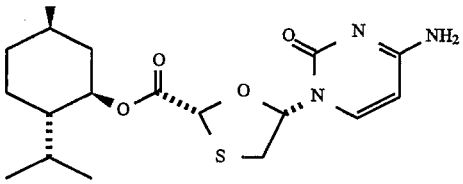

A 12:1 mixture of (1'R,2'S,5'R)-menthyl 5S-(N-4"-acetylcytosin-1"-yl)-oxathiolane-2R-oxathiolane carboxylate (cis isomer) and (1'R,2'S,5'R)-menthyl 5R-(N-4"-acetylcytosin-1"-yl)-oxathiolane-2R-oxathiolane carboxylate (trans isomer) (47 mg,0.11 mmol) was dissolved in dichloromethane (0.5 mL) and 2-propanol (1 mL). Trifluoroacetic acid (0.2 mL) was added to this solution and the resultant mixture was heated at 60° C. for 2 hours and then was kept at room temperature for 14.5 hours. The reaction mixture was diluted with dichloromethane and washed with saturated $NaHCO_3$ solution, water, brine, and then was dried (anhydrous $Na_2SO_4$). The solvent was removed under reduced pressure and the product obtained was dried under vacuum to afford 40 mg (95%) of the title compounds. The $^1$H NMR spectrum of the above material suggested a purity of ≧97%. Based on the signals derived from the $C_6$ hydrogen of the cytosine moiety present in both of the isomers, the 12:1 ratio of the cis [(δ8.38 (d, J=7.3 Hz)] and trans [(δ7.48 (d, J=7.3 Hz)] nucleosides was maintained. The major compound was obtained by fractional crystallization with methanol and displayed physical properties identical to those reported in this example.

EXAMPLE 32

(1'S,2'R,5'S)-MENTHYL-5S-(N-4"-ACETYLCYTOSIN-1"-YL)-1,3-OXATHIOLANE-2R-CARBOXYLATE

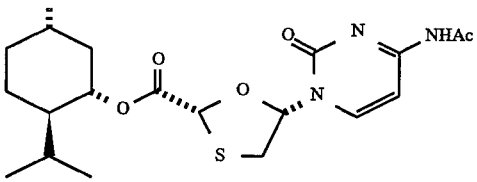

(1'S,2'R,5'S)-menthyl 5R-acetoxy-1,3-oxathiolane-2R-carboxylate (55 mg, 0.166 mmol) in dichloromethane (0.5 mL) and iodotrimethylsilane (0.026 mL, 0.166 mmol) were added to monosilylated N-4-acetylcytosine (59 mg, 0.198 mmol), generated by refluxing N-4-acetylcytosine in 1,1,1,3,3,3-hexamethyldisilazane (HMDS) overnight in the presence of catalytic amount of ammonium sulfate and subsequently removing HMDS, in dichloromethane (0.5 mL) under argon atmosphere at room temperature. The stirring was continued for 19 hours and thin layer chromatography showed almost complete consumption of the starting oxathiolane. The reaction mixture was diluted with dichloromethane, washed with saturated aqueous sodium bicarbonate, aqueous sodium thiosulfate and brine, dried over sodium sulfate, concentrated and dried to afford 70 mg (100%) of crude products. $^1$H NMR suggested cis:trans ratio at 15:1 and the presence of ca. 4.6% of unreacted oxathiolane. $^1$H NMR ($CDCl_3$): 0.78 (d,3H), 0.80–2.10 (m, 15H), 2.27 (s, 3H), 3.12–3.30 (m, 1H) 3.52–3.78 (m, 1H), 4.78 (m, 1H), 5.51 (s, 0896H), 5.60 (s, 0.046H), 5.82 (s, 0.058H), δ6.42 (t, 0.896H), 6.63 (dd, 0.046 H), 6.68 (d, 0.058H), 7.47 (d, 0.954H), 7.77 (d, 0.058H), 8.70 (d, 0.896H). The major compound was isolated by crystallization from methanol or trituration with ethylacetate-ether mixtures.

EXAMPLE 33

(1'S,2'R,5'S)-MENTHYL-5S-(N-4"-ACETYLCYTOSIN-1"-YL)-1,3-OXATHIOLANE-2R-CARBOXYLATE

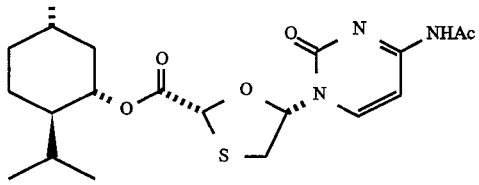

2,6-lutidine (0.023 mL, 0.199 mmol) and trimethylsilyl trifluoromethanesulfonate (0.038 mmol, 0.199 mmol) were added to N-4-acetylcytosine (30.5 mg, 0.199 mmol) in dichloromethane (0.2 mL) at room temperature under argon atmosphere. The mixture was stirred for 20 minutes and a solution of (1'S,2'R,5'S)-menthyl-5S-acetoxy-1,3-oxathiolane-2R-carboxylate (55 mg, 0.166 mmol) in dichloromethane (0.3 mL) and iodotrimethyl-silane (0.026 mL, 0.166 mmol) were introduced successively. The stirring was continued for 2.5 hour and thin layer chromatography showed complete consumption of the starting oxathiolane. The reaction mixture was diluted with dichloromethane, washed with saturated aqueous sodium bicarbonate, aqueous sodium thiosulfate and brine, dried over sodium sulfate, concentrate and dried to afford 70 mg (100%) of crude products. $^1$H NMR suggested cis:trans ratio at 10:1 and no other impurity detectable by the spectrum. $^1$HNMR (CDCl$_3$): 0.78 (d, 3H), 0.80–2.10 (m, 15H), 2.27 (s, 3H), 3.16 (dd, 0.91H), 3.25 (d, 0.09H), 3.63 (dd, 0.91H), 3.74 (dd, 0.09H), 4.78 (m, 1H), 5.51 (s, 0.91H), 5.82 (s, 0.09H); 8 6.42 (t, 0.91H), 6.68 (d, 0.09H), 7.47 (d, 1H), 7.77 (d, 0.09H), 8.70 (d, 0.91H).

EXAMPLE 34

CIS- AND TRANS-ISOPROPYL 5-ACETOXY-1,3-OXATHIOLANE-2-CARBOXYLATE

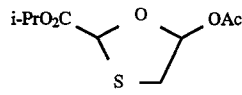

A solution of cis- and trans 5-acetoxy-1,3-oxathiolane-2-carboxylic acid (260 mg, 1.3528 mmol) and isopropanol (0.11 mL, 1.3528 mmol) in dichloromethane (4 mL) at 0° C. was treated with dicyclohexylcarbodiimide (DCC) (279 mg, 1.3528 mmol) in dichloromethane (1 mL) and 4 dimethylaminopyridine (DMAP) (14 mg, 0.135 mmol). The mixture was stirred at room temperature overnight, then diluted with ether and filtered through a Celite® pad. The filtrate was concentrated and the residue was chromatographed on silica gel with ethyl acetate-hexane to give the products as a colorless oil (263 mg, 83%). $^1$H NMR (CDCl$_3$): δ1.26 (6H, d) ; 2.10, 2.11 (3H, s) ; 3.13–3.46 (2H, m); 5.05 (1H, m); 5.60, 5.61 (1H, s); 6.63 (0.54H, m); 6.78 (0.46H, d).

EXAMPLE 35

CIS-ISOPROPYL-5-(CYTOSIN-1'-YL)-1,3-OXATHIOLANE-2-CARBOXYLATE

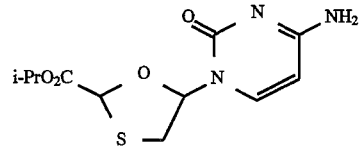

2,4,6-collidine (0.23 mL, 1.74 mmol) and t-butyl-dimethylsilyl trifluoromethanesulfonate (0.4 mL, 1.74 mmol) were added to a suspension of cytosine (96.7 mg, 0.87 mmol) in dichloromethane (0.8 mL) at room temperature under argon atmosphere. The mixture was stirred for 25 minutes and a solution of cis:trans (1.2:1) isopropyl 5-acetoxy-1,3-oxathiolane-2-carboxylate (168 mg, 0.717 mmol) in dichloromethane (0.8 mL) and a solution of iodotrimethylsilane (0.114 mL, 0.788 mmol) were introduced successively. Stirring was continued for one hour and the reaction mixture was diluted with dichloromethane, washed with saturated aqueous sodium thiosulfate, water and brine, dried over sodium sulfate and concentrated. The residue was triturated with ether-hexane (1:1, 7 mL) and saturated aqueous sodium bicarbonate (1.5 mL). The aqueous layer was removed and the remaining mixture was centrifuged.

The solid was washed twice with hexanes and the washings were combined with centrifugate, washed with 1N HCl, water and brine, dried and concentrated to give the unreacted starting material in virtually pure form (64 mg, 38%, cis:trans=1:9). The white solid was dried and gave the products as a cis:trans mixture in 12:1 ratio (122.6 mg, 60%). $^1$H NMR (CDCl$_3$): δ1.30 (t, 6H), 3.11 (dd, 1H), 3.52 (dd, 1H), 5.11 (m, 1H), 5.45 (s, 1H), 5.82 (d, 1H), 6.47 (dd, 0.92H), 6.72 (m, 0.08H), 7.49 (d, 0.08H), 8.32 (d, 0.92H).

EXAMPLE 36

CIS- AND TRANS-T-BUTYL 5-ACETOXY-1,3-OXATHIOLANE-2-CARBOXYLATE

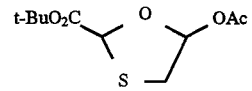

A solution of cis- and trans-5-acetoxy-1,3-oxathiolane-2-carboxylic acid (176 mg, 0.915 mmol) and t-butanol (0.095 mL, 0.915 mmol) in dichloromethane (4 mL) at 0° C. was treated with DCC (207 mg, 1 mmol) in dichloromethane (1 mL) and DMAP (11 mg, 0.09 mmol). The mixture was stirred at room temperature overnight, then diluted with ether and filtered through a Celite® pad. The filtrate was concentrated and the residue was chromatographed on silica gel with ethyl acetate-hexane to give the products as a colorless oil (175 mg, 77%). $^1$H NMR (CDCl$_3$): δ1.46 (9H, d); 2.07, 2.09 (3H, s); 3.10–3.44 (2H, m); 5.50, 5.52 (1H, s); 6.60 (0.42H, m); 6.74 (0.58H, d).

EXAMPLE 37

CIS-T-BUTYL-5-(CYTOSIN-1'-YL)-1,3-OXATHIOLANE-2-CARBOXYLATE

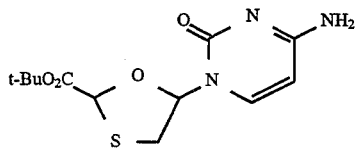

2,4,6-collidine (0.187 mL, 1.4 mmol)' and t-butyldimethylsilyl trifluoromethanesulfonate (0.325 mL, 1.4 mmol) were added to a suspension of cytosine (78.6 mg, 0.7 mmol) in dichloro-methane (0.6 mL) at room temperature under argon atmosphere. The mixture was stirred for 25 minutes and a mixture of cis and trans (1:1.4) t-butyl 5-acetoxy-1,3-oxathiolane-2-carboxylate (146.5 mg, 0.59 mmol) in dichloromethane (0.6 mL) and iodotrimethylsilane (0.092 mL, 0.65 mmol) were introduced successively. Stirring was continued for one hour and the reaction mixture was diluted with dichloromethane, washed with saturated aqueous sodium thiosulfate, water and brine, dried over sodium sulfate and concentrated. The residue was triturated with ether-hexanes (1:1, 7 mL) and saturated aqueous sodium bicarbonate (1.5 mL). The aqueous layer was removed and the remaining mixture was centrifuged. The solid was washed twice with hexanes and the washings were combined with the centrifugate, washed with 1N HCl, water and brine, dried and concentrated to give the unreacted starting material in virtually pure form (77 mg, 52.6%, cis:trans=1:11). The white solid was dried and gave the products as a cis:trans mixture in 16:1 ratio (82.6 mg, 46.4%). $^1$H NMR (CDCl$_3$): δ1.50, 1.52 (s, 9H), 3.12 (dd, 0.94H), 3.20 (dd, 0.06H), 3.52 (dd, 0.94H), 3.72 (dd, 0.06H), 5.37 (s, 0.94H), 5.75 (s, 0.06H), 5.83 (d, 1H), 6.44 (dd, 0.94H), 6.71 (d, 0.06H), 7.49 (d, 0.06H), 8.38 (d, 0.98H).

EXAMPLE 38

CIS- AND TRANS-2-N,N-DIETHYLAMINOCARBONYL-5-ACETOXY-1,3-OXATHIOLANE

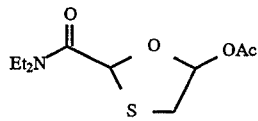

A solution of cis- and trans-5-acetoxy-1,3-oxathiolane-2-carboxylic acid (119 mg, 0.62 mmol) and diethylamine (0.07 mL, 0.68 mmol) in dichloromethane (2 mL) at 0° C. was treated with DCC (140 mg, 0.68 mmol) in dichloromethane (1 mL) and DMAP (7.6 mg, 0.06 mmol). The mixture was stirred at room temperature overnight, then diluted with ether and filtered through a Celite® pad. The filtrate was concentrated and the residue was chromatographed on silica gel with ethyl acetate-hexane to give the products as a colorless oil (84.5 mg, 55%). $^1$H NMR (CDCl$_3$): δ1.10, 1.40 (6H, t); 2.07, 2.10 (3H, s); 3.15–3.56 (6H, m); 5.80, 5.87 (1H, s); 6.58 (0.53H, m); 6.83 (0.47H, d).

EXAMPLE 39

CIS-2-N,N-DIETHYLAMINOCARBONYL-5-(CYTOSIN-1'-YL)-1,3-OXATHIOLANE

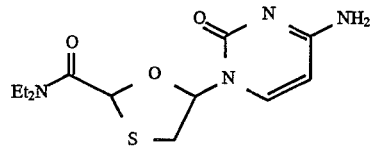

2,4,6-collidine (0.108 mL, 0.82 mmol) and t-butyldimethylsilyl trifluoromethanesulfonate (0.188 mL, 0.82 mmol) were added to a suspension of cytosine (45.5 mg, 0.41 mmol) in dichloromethane (0.4 mL) at room temperature under argon atmosphere. The mixture was stirred for 25 minutes and a mixture of cis and trans (1.12:1) 2-N,N-diethylamindocarbonyl-5-acetoxy-1,3-oxathiolane (84 mg, 0.34 mmol) in dichloromethane (0.4 mL) and a solution of iodotrimethylsilane (0.053 mL, 0.375 mmol) were introduced successively. Stirring was continued for one hour and the reaction mixture was diluted with dichloromethane, washed with saturated aqueous sodium thiosulfate, water and brine, dried over sodium sulfate and concentrated. The residue was triturated with ether-hexane (1:1, 7 mL) and saturated aqueous sodium bicarbonate (1.5 mL). The aqueous layer was removed and the remaining mixture was centrifuged. The solid was washed twice with hexanes and the washings were combined with centrifugate, washed with 1N HCl, water and brine, dried and concentrated to give the unreacted starting material in virtually pure form (17 mg, 20%, trans only). The white solid was dried to give the products as a cis:trans mixture in 24:1 ratio (47.5 mg, 47.5%). $^1$H NMR (DMSO-d$_6$): δ1.04 (t, 3H, J=7 Hz), 1.12 (t, 3H, J=7 Hz), 3.17 (dd, 1H, J=5 Hz, 9 Hz), 3.30 (m, 4H), 3.53 (dd, 1H, J=5 Hz, 9 Hz), 5.74 (d, 1H, J=7 Hz), 5.96 (s, 1H), 6.28 (t, 0.96H, J=5 Hz), 6.62 (m, 0.04H), 7.16 (b.s., NH), 7.22 (b.s., NH), 7.60 (d, 0.04H), 8.46 (d, 0.96H, J=7 Hz).

EXAMPLE 40

1'S,2'R,5'S)-MENTHYL-1,3-OXATHIOLANE-2R-CARBOXYLATE

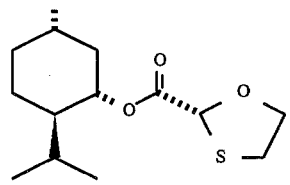

To a mixture of (1'S,2'R,5'S)-menthyl-5R-acetoxy-1,3-oxathiolane-2R-carboxylate (2.01 g, 6.08 mmol) and triethylsilane (9.67 mL, 60.05 mmol) at room temperature under argon atmosphere was added trimethylsilyl trifluoromethanesulfonate (1.17 mL, 6.04 mmol). The reaction mixture was stirred at room temperature for 12 hours, then diluted with dichloromethane, washed with saturated aqueous solution of sodium bicarbonate, dried over anhydrous sodium sulfate, and evaporated to dryness in vacuo to afford crude product. Subsequent chromatography on silica gel using hexane-ethyl acetate as eluate gave the product as colourless oil (1.33 g, 80.5%) $^1$H NMR (CDCl$_3$): δ0.75–2.10 (m, 15H), 2.97–3.20 (m, 2H), 4.2014.40 (m, 2H), 4.72 (dr, 1H), 5.45 (s, 1H) [α]$_D$+104° (c 1.16, CHCl$_3$).

EXAMPLE 41

(1'S,2'R,5'S)-MENTHYL-4R-HYDROXY-1,3-OXATHIOLANE-2R-CARBOXYLATE AND (1'S,2'R,5'S)-MENTHYL-4S-HYDROXY-1,3-OXATHIOLANE-2R-CARBOXYLATE

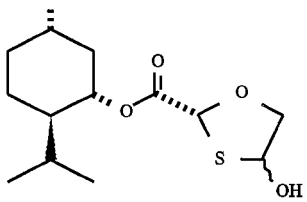

A mixture of (1'S,2'R,5'S)-menthyl-1,3-oxathiolane-2R-carboxylate (0.500 g, 1.84 mmol) and benzoylperoxide (0.489 g, 97%, 1.96 mmol) in 20 mL benzene was heated to reflux for 6 hours. The organic solvent was removed in vacuo and the residue was diluted with dichloromethane, washed with saturated aqueous solution of sodium bicarbonate, dried over anhydrous sodium sulfate, and evaporated to dryness in vacuo to afford crude benzoate product. Subsequent chromatography by using hexane-ethyl acetate as eluate gave the benzoate as a solid (0.21 g, 30.3%). The mixture of the benzoate (0.200 g, 0.531 mmol) and potassium carbonate (0.073 g, 0.532 mmol) in THF—MeOH—$H_2O$ (4 mL/5 mL/2 mL) was stirred at 0° C. for 7 hours and organic solvent was removed in vacuo. The residue was diluted with $H_2O$ (7 mL), extracted with ether (10 mL), acidified with aqueous HCl, and extracted with dichloromethane. The dichloromethane layer was dried over sodium sulfate and evaporated to dryness in vacuo to afford crude product. Subsequent chromatography using hexane ether as eluent gave the product as a solid (67 mg, 43.7%) $^1$H NMR (CDCl$_3$): δ0.75–2.10 (m, 15H), 4.03–4.83 (m, 2H), 5.52–5.75 (m, 2H).

EXAMPLE 42

(1'S,2'R,5'S)-MENTHYL-4R-CHLORO-1,3-OXATHIOLANE-2R-CARBOXYLATE AND (1'S,2'R,5'S)-MENTHYL-4S-CHLORO-1,3-OXATHIOLANE-2R-CARBOXYLATE

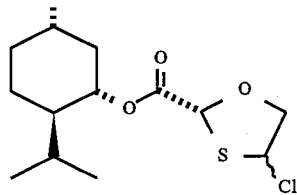

To a mixture of (1'S,2'R,5'S)-menthyl-4R-hydroxy-1,3-oxathiolane-2R-carboxylate and (1,S,2'R,5'S)-menthyl-4S-hydroxy-1,3-oxathiolane-2R-carboxylate (40mg, 0.138 mmol) and methytrifluoromethansulfonyl chloride (18.24 μL, 0.239 mmol) in dichloromethane (5 mL) at room temperature under argon atmosphere was added triethylamine (57.99 mL, 0.416 mmol). The reaction mixture was stirred at room temperature for 2 hours then diluted with dichloromethane, washed with saturated aqueous solution of sodium bicarbonate, dried over anhydrous sodium sulfate, and evaporated to dryness in vacuo to afford crude product. Subsequent chromatography by using hexane ether as eluent gave the product as two diastereomers (18 mg, 42.3%, 14.6 mg, 34.2%) epimeric at C4. $^1$H NMR CDCl$_3$): δ0.75–2.05 (m, 15H), 4.55 (m, 1H), 4.69 (m, 1H), 5.75 (m, 1H), 5.80 (m, 1H); δ0.75–2.10 (m, 15H), 4.33 (m, 1H), 4.78 (m, 1H), 5.56 (s, 1H), 5.68 (m, 1H).

EXAMPLE 43

CIS 2-CARBOETHOXY-4-ACETOXY-1,3-DIOXOLANE

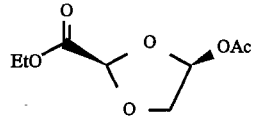

A 2.5:1 mixture of cis and trans-2-carboethoxy-4-acetyl-1,3-dioxolane (406 mg, 2.16 mmol), 85% meta-chloroperbenzoic acid (mCPBA) (68 mg, 3.81 mmol) and sodium carbonate (389 mg, 3.67 mmol) in dry dichloromethane (10 mL) was stirred under argon for. 16 hours at room temperature. The resultant suspension was diluted with dichloromethane and water and stirred for 10 minutes. The aqueous phase was removed and the organic phase was washed successively with saturated sodium thiosulfate, water, brine and then was dried over anhydrous magnesium sulfate. The solvent was removed under reduced pressure and the crude product thus obtained was subjected to flash column chromatography (30% EtOAc-Hexanes) to give the title compound (11% yield) which displayed the following spectral characteristics; $^1$H NMR (CDCl$_3$): δ1.31 (t, 3H, J=7.2 Hz), 2.07 (s, 1H), 4.15 (d of d, 1H, J=4.5, 9.1 Hz), 4.21–4.29 (m, 3H), 5.42 (s, 1H), 6.39 (d of d, 1H, J=2.4, 4.5 Hz); $^{13}$C NMR (CDCl$_3$): δ14.05, 20.97, 29.69, 71.34, 94.04, 99.80, 167.19, 170.11.

EXAMPLE 44

TRANS 2-CARBOETHOXY-4-ACETOXY-1,3-DIOXOLANE

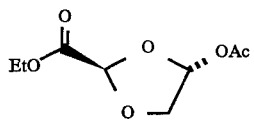

A 2.5:1 mixture of cis and trans-2-carboethoxy-4-acetyl-1,3-dioxolane (406 mg, 2.16 mmol), 85% mCPBA (68 mg, 3.81 mmol) and sodium carbonate (389 mg, 3.67 mmol) in dry dichloromethane (10 mL) was stirred under argon for 16 hours at room temperature. The resultant suspension was diluted with dichloromethane and water and stirred for 10 minutes. The aqueous phase was removed and the organic phase was washed successively with saturated sodium thiosulfate, water, brine and then was dried over anhydrous magnesium sulfate. The solvent was removed under reduced pressure and the crude product thus obtained was subjected to flash column chromatography (30% EtOAc-Hexanes) to give the title compound (49% yield) which displayed the following spectral characteristics; $^1$H NMR (CDCl$_3$): δ1.29 (t, 3H, J=7.2 Hz), 2.09 (s, 1H), 4.12 (d of d, 1H, J=0.9, 9.1 Hz), 4.19–4.31 (m, 3H), 5.53 (s, 1H), 6.48 (d of d, 1H, J=0.9, 3.9 Hz).

EXAMPLE 45

CIS AND TRANS 2-CARBOETHOXY-4-(THYMIN-1'-YL)-1,3-DIOXOLANE

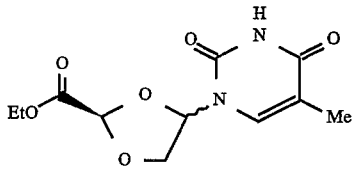

To a stirred suspension of thymine (44.5 mg, 0.353 mmol) in dichloromethane (1 mL) containing 2,6-lutidine (82 μL, 0.706 mmol) under an argon atmosphere was added trimethylsilyl trifluoromethanesulphonate (136 μL, 0.706 mmol). The resulting mixture was stirred for 15 minutes to give a homogeneous solution. A solution of the substrate, ethyl 4-acetoxy-1,3-dioxolane-2-carboxylate (60 mg, 0.294 mmol) in dichloromethane (1 mL) and iodotrimethylsilane (42 μL, 0.294 mmol) was sequentially introduced into the above solution. The reaction mixture was stirred at room temperature for 5 hours and then was quenched with a half-saturated solution of $Na_2S_2O_3$ (2 mL), followed by dilution with dichloromethane (5 mL). The resulting mixture was stirred for 5 minutes and then was transferred to a separatory funnel with the aid of more dichloromethane. The aqueous phase was removed and the organic layer was washed with saturated $Na_2S_2O_3$, water, 1M HCl, brine and then was dried ($Na_2SO_4$). The solvent was removed under reduced pressure to provide the crude product. This material was suspended in dichloromethane (~1.5 mL) and then was triturated with a 1:1 mixture of EtOAc-Hexane (~6 mL) to give 25 mg of the cis nucleoside as a white solid; $^1$H NMR (DMSO de): δ1.23 (t, 3H, J=7.1 Hz), 1.78 (d, 3H, J=1 Hz), 4.15–4.30 (m, 4H), 4.38 (d of d, 1H, J=2.3, 9.8 Hz), 5.33 (s, 1H), 6.33 (d of d, 1H, J=2.3, 5.8 Hz), 7.52 (d, 1H, J=1.1, Hz), 11.42 (br s, 1H). The triturate was concentrated and subjected to column chromatography (70% EtOAc-Hexane) to afford 26 mg of the two nucleoside as a 1:1 mixture; $^1$H NMR (CDCl$_3$): δ1.33 (t, 1.5H, J=7.2 Hz), 1.35 (t, 1.5H, J=7.2 Hz), 1.91–1.99 (two overlapping d, 3H), 4.16 (d of d, 0.5H, J=1. 9, 9.7 Hz), 4.20–4.38 (m, 3H), 4.53 (d of d, 0.5H, J=5.8, 9.7 Hz), 5.30 (s, 0.5H), 5.72 (s, 0.5H), 6.44 (d of d, 0.5H, J=3.3, 5.4 Hz), 6.60 (d of d, 0.5H, J=2.0, 5.8 Hz), 7.10 (d, 0.5H, J=1.3 Hz), 7.75 (d, 0.5H, J=1.3 Hz), 9.40 (br s, 0.5H), 9.43 (br s, 0.5H).

EXAMPLE 46

CIS AND TRANS 2-CARBOETHOXY-4-(N-4'-ACETYLCYTOSIN-1'-YL)-1,3-DIOXOLANE

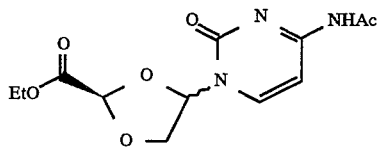

To a stirred suspension of N-acetylcytosine (66 mg, 0.430 mmol) in dry $CH_2Cl_2$ (1.5 mL) under an argon atmosphere was added, successively, 2,6-lutidine (100 μL, 0.859 mmol) and trimethylsilyl trifluoromethanesulphonate (166 μL, 0.859 mmol). The resultant mixture was stirred for 25 minutes to produce a homogeneous solution. A solution of a 4:1 mixture of cis and trans-2-carboethoxy-4-acetoxy-1,3-dioxolane (73 mg, 0.358 mmol) in $CH_2Cl_2$ (1 mL) was then introduced, followed by iodotrimethylsilane (51 μL, 0.358 mmol). The reaction was allowed to proceed for 16 hours and then was quenched with saturated sodium thiosulfate. The resulting mixture was diluted with $CH_2Cl_2$ and was washed successively with saturated sodium thiosulfate, water, brine, and then was dried over anhydrous magnesium sulfate. Removal of the solvent under reduced pressure gave the crude product which was purified by flash column chromatography (2% MeOH—EtOAc) to afford 44% of the title compounds as a 3:1 mixture of the cis and trans isomers; $^1$H NMR (CDCl$_3$): δ1.34 (t, 3H, J=7.0 Hz), 2.28 (s, 0.75H), 2.29 (s, 0.25H), 4.21–4.35 (m, 3H), 4.36 (d of d, 0.75 H, J=5.2, 9.9 Hz), 4.59 (d of d, 0.25H, J=5.2, 9.9 Hz), 5.39 (s, 0.75H), 5.77 (s, 0.25H), 6.24 (d of d, 0.75H, J=2.8, 5.1 Hz), 6.39 (d of d, 0.25H, J=1.7, 5.1 Hz), 7.49 (2 overlapping doublets, 1H), 7.79 (d, 0.25H, J=7.6 Hz), 8.40 (d, 0.75H, J=7.6 Hz), 9.95 (br s, 1H).

EXAMPLE 47

(±)-CIS AND TRANS-5-ACETOXY-1,3-OXATHIOLANE-2-CARBOXYLIC ACID

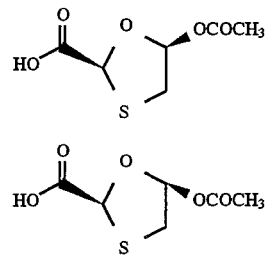

Trans-5-hydroxy-1,3-oxathiolane-2-carboxylic acid (250 g, 1.67 mol) was added, in portions, to a stirred solution of acetic anhydride (0.625 L, 6.62 mol) and methanesulphonic acid (5 mL, 77 mmol) at room temperature. The resultant clear solution was stirred at room temperature for 60 minutes, slowly added to stirred aqueous 0.03M sodium bicarbonate solution (2.5L) and then the mixture was stirred for a further 60 minutes. Sodium chloride (750 g, 12.83 mol) was added and the mixture was stirred for a further 30 minutes, clarified, and then extracted with isopropyl acetate (1×1.25 L, 3×0.625 L). The combined extracts were concentrated to 1.25 L under reduced pressure. Xylene (2.5 L) was added and the mixture reconcentrated to 1.25 L under reduced pressure. The xylene addition/reconcentration procedure was repeated and the resultant suspension was cooled to room temperature and stirred for 18 hours. The solid was collected by vacuum filtration, washed with xylene (2×0.25 L) and dried, in vacuo, at 40°–45° to give the title compound (265 g, 83%) which was shown, by comparison of $^1$H NMR spectra, to be a 65:35 mixture of the compounds of Examples 3 and 4.

EXAMPLE 48

5R-ACETOXY-1,3-OXATHIOLANE-2R-CARBOXYLIC ACID, SALT WITH 1S,2R-α-(1-AMINOETHYL) BENZENEMETHANOL (1:1)

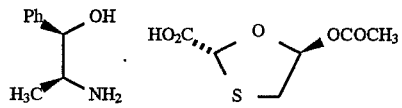

a) A solution of 1S,2R-α-(1-aminoethyl) benzenemethanol (125.9 g, 0.83 mol) in isopropyl acetate (0.5 L) was added to a stirred solution of (±) cis-/trans-5-acetoxy-1,3-oxathiolane-2-carboxylic acid (Example 47; 400 g, 2.08 mol), in isopropyl acetate (4.2 L), at room temperature under a nitrogen atmosphere. The resultant solution was stirred for 10 minutes, seeded with authentic product (0.4 g) and stirred for a further 4 hours at room temperature. The suspension was stirred at 15°–18° for 17 hours and the solid was collected by vacuum filtration, washed with isopropyl acetate (1 x. 0.4 L, 1×0.2 L) and dried, in vacuo, at 45° to give the title compound (205.9 g, 28%). [α]$_D$+34° (MeOH), mp 151°–2° (decomp), δ(DMSO-D$_6$) 0.91 (d, 3H, J=6.8 Hz), 2.05 (s, 3H), 3.04 (d, 1H, J=11 Hz), 3.32 (dd, 1H, J=4.2 Hz), 3.40 (dg, 1H, J=6.8, 2.4 Hz), 4.97 (d, 1H, J=2.4 Hz), 5.34 (s, 1H), ca. 6.4 (br, 1H), 7.2–7.4 (m, 5H), ca. 8.3 (br, 3H).

b) A solution of 1S,2R-α-(1-aminoethyl)benzenemethanol (177 mg, 1.17 mmol) in isopropyl acetate (1 mL) was added to a stirred solution of (±)-trans-5-acetoxy-1,3-oxathiolane-2-carboxylic acid (500 mg, 2.60 mmol) in isopropyl acetate (6 mL) at 25°–30°, and further isopropyl acetate (0.5 mL) was added. Crystallisation commenced after 5 minutes. The suspension was stirred at 25°–30° for 18 hours and then the solid was collected by vacuum filtration, washed with isopropyl acetate (1 mL) and dried, in vacuo, at 40° to give the title compound (353 mg, 40%), as shown by comparison of its $^1$H NMR spectrum with that of part (a).

EXAMPLE 49

(−)-TRANS-5-ACETOXY-1,3-OXATHIOLANE-2-CARBOXYLIC ACID

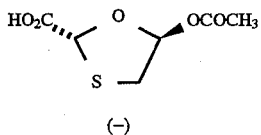

(−)

5 M-Aqueous hydrochloric acid (126 mL, 0.63 mol) was added to a stirred suspension of the compound of Example 48 (180 g, 0.52 mol) in saturated aqueous sodium chloride (414 mL) at room temperature. The mixture was stirred at room temperature for 30 minutes, cooled to 10° and stirred at this temperature for a further 30 minutes. The solid was collected by vacuum filtration, washed with chilled water (2×90 mL) and dried, in vacuo, at 33° to give the title compound (81.3 g, 81%).

EXAMPLE 50

(1'R,2'S,S'R)-MENTHTL-5R ACETOXY-1,3-OXATHIOLANE-2R-CARBOXYLATE

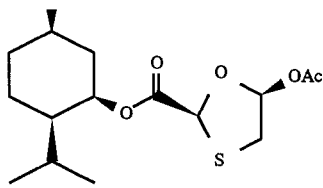

a) A solution of oxalyl chloride (66.5 g, 0.52 mol) in dichloromethane (120 mL) was added over 30 minutes to a stirred cold (−5°) mixture of N,N-dimethylformamide (32 mL) and dichloromethane (240 mL), and the suspension formed was stirred at −5° to 0° for 30 minutes. The compound of Example 49 (80 g, 0.42 mol) was added in portions and the resultant yellow solution was stirred at 0° for 45 minutes. This solution was added over 60 minutes to a stirred, cold (−5°) solution of (1R,2S,5R)-(−)-menthol (65.2 g, 0.425 mol) in dichloromethane (200 mL) and pyridine (84 mL, 1.04 mol) and the resultant suspension was stirred at 0°–5° for a further 2 hours.

The reaction mixture was washed with 2 M-aqueous hydrochloric acid (1×240 mL, 1×160 mL) and the combined aqueous acidic washes were back extracted with dichloromethane (160 mL). The organic phases were combined, clarified, and concentrated in vacuo to c.a. 240 mL, 2,2,4-trimethylpentane (400 mL) was added and the solution concentrated, in vacuo, to 240 mL. Crystallisation of the product occurred during the distillation. Further 2,2,4-trimethylpentane (400 mL) was added and the mixture concentrated to c.a. 700 mL. The stirred suspension was then cooled to 5° and aged for 60 minutes. The solid was collected by vacuum filtration, washed with 2,2,4-trimethylpentane (2×80 mL) and dried, in vacuo, at 33° to give the title compound (93.2 g, 68%) as shown by comparison of the $^1$H NMR spectrum with that of Example 8.

b) Oxalyl chloride (102 g, 0.80 mol) was added over 20 minutes to a stirred, cold (−10°) mixture of N,N-dimethylformamide (63 μL) and dichloromethane (840 mL) and the suspension formed was stirred at −10° to −6° for 15 minutes. The compound of Example B (140 g, 0.728 mol) was added and the resultant pale yellow solution was stirred at −8° for 20 minutes. (1R,2S,5R)-(−)-Menthol (126 g, 0.80 mol) was added followed by pyridine (140 mL, 1.73 mol), added over 50 minutes. The suspension formed was stirred at −9° for 18 hours and then 1M aqueous hydrochloric acid (280 mL) was added. The separated aqueous acid phase was extracted with dichloromethane (140 mL) and the combined organic phases were washed with 1M aqueous hydrochloric acid (280 mL). The aqueous phase was back extracted with dichloromethane (140 mL) and the combined organic phases were washed with a solution containing sodium hydrogen carbonate (5.6 g) and sodium chloride (28 g) in water (266 mL). The aqueous phase was back extracted with dichloromethane (140 mL) and the combined organic phases were clarified and concentrated to 560 mL by distillation at atmospheric pressure. 2,2,4-Trimethylpentane (700 mL) was added and the solution was concentrated, in vacuo, to 700 mL. The 2,2,4-trimethylpentane addition/reconcentration procedure was repeated, and the resultant solution was cooled to 17° (seeded with authentic product (0.7 g) at 34° and 23°). The suspension was stirred at 17° for 2 hours and the solid was collected by vacuum filtration, washed with 2,2,4-trimethylpentane (2×70 mL) and dried, in vacuo, at 43° to give the title compound (332 g, 14%) as shown by comparison of the $^1$H NMR spectrum with that of Example 8).

While we have presented a number of embodiments of our invention, many alternatives, modifications and variations of these embodiments will be apparent to those of ordinary skill in the art. Therefore, it will be appreciated that the scope of this invention is to be defined by the following claims, rather than the specific examples presented above.

We claim:

1. A process for producing an intermediate of formula (IIa) or formula (IIb)

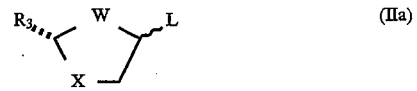

-continued

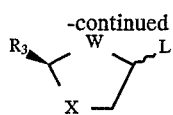
(IIb)

wherein W is S, S=O, SO$_2$, or O;

X is S, S=O, SO$_2$, or O;

R$_3$ is a substituted carbonyl or carbonyl derivative; and

L is a leaving group, comprising the step of resolving a mixture of the two compounds using a chiral auxiliary.

2. A method of preparing a compound of formula (IIa') or formula (IIb'):

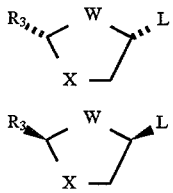
(IIa')

(IIb')

wherein W is S, S=O, SO$_2$, or O;

X is S, S=O, SO$_2$, or O;

R$_3$ is a substituted carbonyl or carbonyl derivative; and

L is a leaving group;

comprising the step of resolving a mixture of the two compounds by means of a chiral auxiliary.

3. A method of preparing a compound of formula (IIa") or formula (IIb"):

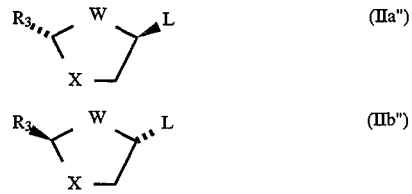
(IIa")

(IIb")

wherein W is S, S=O, SO$_2$, or O;

X is S, S=O, SO$_2$, or O:

R$_3$ is a substituted carbonyl or carbonyl derivative; and

L is a leaving group;

comprising the step of resolving a mixture of the two compounds by means of a chiral auxiliary.

* * * * *